United States Patent
Taniguchi

(10) Patent No.: US 11,602,261 B2
(45) Date of Patent: Mar. 14, 2023

(54) ENDOSCOPE VALVE

(71) Applicant: OLYMPUS CORPORATION, Tokyo (JP)

(72) Inventor: Yuko Taniguchi, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 1120 days.

(21) Appl. No.: 16/224,927

(22) Filed: Dec. 19, 2018

(65) Prior Publication Data

US 2019/0125167 A1 May 2, 2019

Related U.S. Application Data

(63) Continuation of application No. PCT/JP2017/008829, filed on Mar. 6, 2017.

(30) Foreign Application Priority Data

Jun. 29, 2016 (JP) .............................. JP2016-129301

(51) Int. Cl.
*A61B 1/00* (2006.01)
*A61B 1/015* (2006.01)
(Continued)

(52) U.S. Cl.
CPC ...... *A61B 1/00101* (2013.01); *A61B 1/00066* (2013.01); *A61B 1/00068* (2013.01);
(Continued)

(58) Field of Classification Search
CPC ........................... A61B 1/00068; A61B 1/015
See application file for complete search history.

(56) References Cited

U.S. PATENT DOCUMENTS

| 10,898,062 B2* | 1/2021 | Wolfe ................ A61B 1/00137 |
| 2010/0049001 A1* | 2/2010 | Yamane ................ A61B 1/015 |
| | | 600/159 |

(Continued)

FOREIGN PATENT DOCUMENTS

| CN | 103006167 A | 4/2013 |
| JP | 2007014439 A | 1/2007 |

(Continued)

OTHER PUBLICATIONS

Chinese Office Action dated Oct. 9, 2020 received in CN 201780040187.X.
Japanese Office Action dated Sep. 10, 2019 in Japanese Patent Application No. 2018-524885.
International Search Report dated May 16, 2017 issued in PCT/JP2017/008829.

*Primary Examiner* — Matthew J Kasztejna
(74) *Attorney, Agent, or Firm* — Scully, Scott, Murphy & Presser, P.C.

(57) ABSTRACT

An endoscope button for an endoscope including a cylinder communicating with tubes includes: a first unit and a second unit that are attachable and detachable with respect to a fitting part fixed to the cylinder, and that are separable from each other in a state being removed from the fitting part. The first unit has a cylindrical shape, and includes a cylindrical member that is attachable and detachable with respect to the fitting part. The second unit includes: a fixing member that is inserted inside the cylindrical member in a state in which the endoscope button is attached to the fitting part, and is fixed to the cylindrical member; and a first movable member that is installed movably with respect to the fixing member, and that is movable back and forth inside the cylinder in the state in which the endoscope button is attached to the fitting part.

10 Claims, 20 Drawing Sheets

(51) Int. Cl.
*A61B 8/12* (2006.01)
*A61B 8/00* (2006.01)
*A61B 1/06* (2006.01)

(52) U.S. Cl.
CPC ............ *A61B 1/015* (2013.01); *A61B 1/0661* (2013.01); *A61B 8/12* (2013.01); *A61B 8/4416* (2013.01); *A61B 1/00082* (2013.01); *A61B 1/00091* (2013.01); *A61B 1/00094* (2013.01); *A61B 1/00096* (2013.01); *A61B 8/445* (2013.01); *A61B 8/4461* (2013.01); *A61B 8/4488* (2013.01)

(56) References Cited

U.S. PATENT DOCUMENTS

| | | | |
|---|---|---|---|
| 2012/0088975 | A1 | 4/2012 | Morimoto |
| 2015/0144215 | A1* | 5/2015 | Bellofatto ........... F16K 11/0712 137/625.69 |
| 2015/0148608 | A1* | 5/2015 | Fukushima ........ A61B 1/00094 600/116 |

FOREIGN PATENT DOCUMENTS

| | | | |
|---|---|---|---|
| JP | 2007111266 | A | 5/2007 |
| JP | 2009039463 | A | 2/2009 |
| JP | 2012081083 | A | 4/2012 |
| JP | 2013-070702 | A | 4/2013 |

* cited by examiner

ENDOSCOPE VALVE

CROSS-REFERENCE TO RELATED APPLICATION

This application is a continuation of PCT International Application No. PCT/JP2017/008829 filed on Mar. 6, 2017 which claims the benefit of priority from Japanese Patent Application No. 2016-129301, filed on Jun. 29, 2016, the entire contents of which are incorporated herein by reference.

BACKGROUND

The present disclosure relates to an endoscope button.

Ultrasound endoscopes to observe the inside of a body of a subject by inserting a flexible elongated insertion portion into the body of the subject, and by transmitting and receiving ultrasonic waves by ultrasound transducers that are proved on a distal end side of the insertion portion have been known (for example, Japanese Laid-open Patent-Publication No. 2007-14439).

In the ultrasound endoscope described in Japanese Laid-open Patent-Publication No. 2007-14439, plural tubes (channel suction tube, balloon suction tube, and suction source tube) enabling fluid to flow through, a cylinder that communicate with the tubes, a fitting part (fixing nut) that is fixed to the cylinder, and an endoscope button to switch a connection state of the tubes by depression operation are provided.

SUMMARY

According to one aspect of the present disclosure, there is provided an endoscope button for an endoscope including a cylinder communicating with tubes, the endoscope button including: a first unit and a second unit that are attachable and detachable with respect to a fitting part that is fixed to the cylinder, and that are separable from each other in a state being removed from the fitting part, wherein the first unit has a cylindrical shape, and includes a cylindrical member that is attachable and detachable with respect to the fitting part, the second unit includes: a fixing member that is inserted inside the cylindrical member in a state in which the endoscope button is attached to the fitting part, and is fixed to the cylindrical member; and a first movable member that is installed movably with respect to the fixing member, and that is movable back and forth inside the cylinder in the state in which the endoscope button is attached to the fitting part.

The above and other features, advantages and technical and industrial significance of this disclosure will be better understood by reading the following detailed description of presently preferred embodiments of the disclosure, when considered in connection with the accompanying drawings.

DETAILED DESCRIPTION

An embodiment to implement the present disclosure is explained below with reference to the drawings. The embodiment explained below is not intended to limit the present disclosure. Moreover, like reference symbols are assigned to like parts throughout the drawings.

General Configuration of Endoscope System

Figure 1:
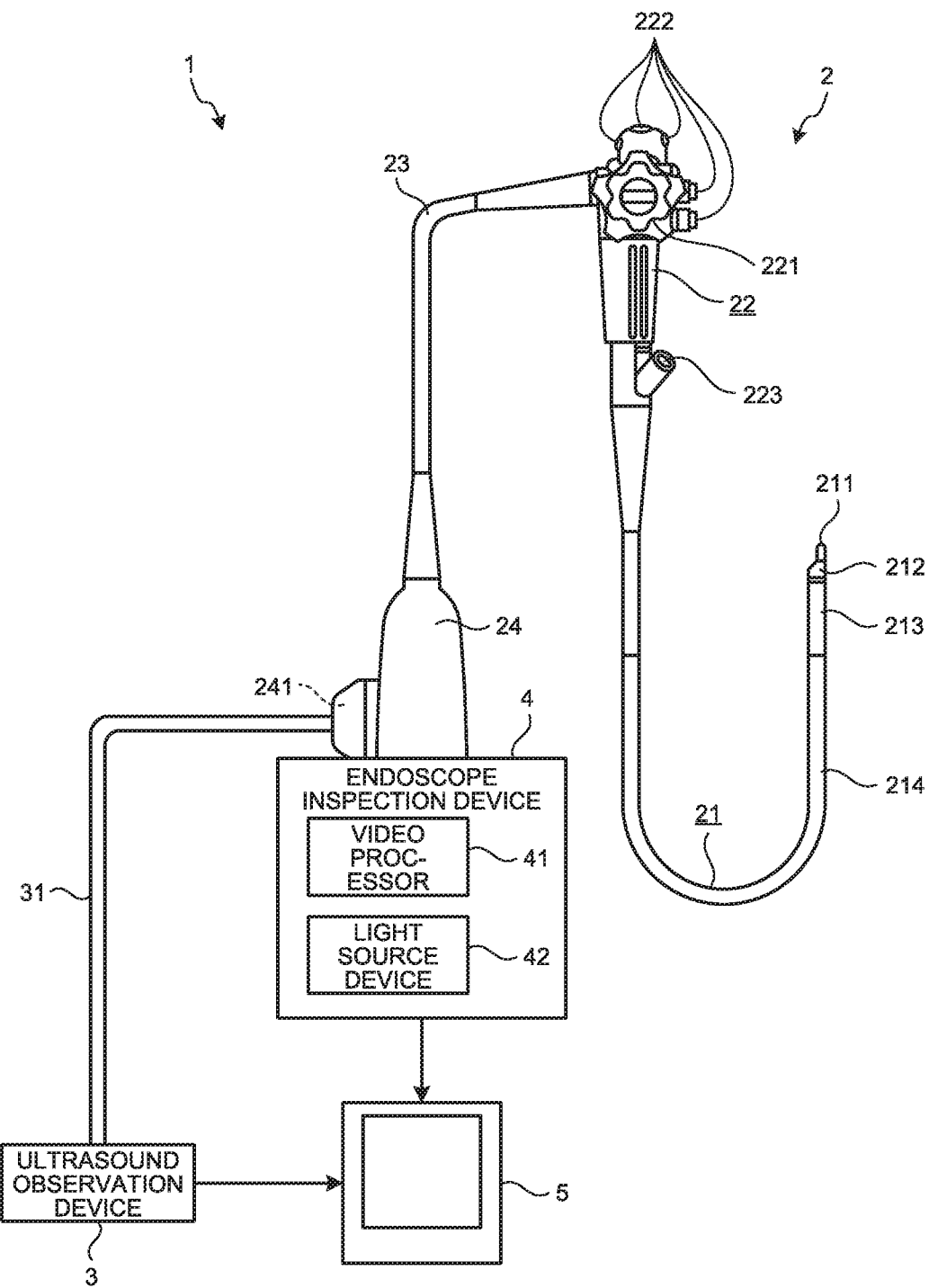
FIG. 1 is a schematic diagram of an endoscope system according to an embodiment.

FIG. 1 is a schematic diagram of an endoscope system 1 according to an embodiment.

The endoscope system 1 is a system that performs ultrasound diagnosis inside the body of a subject, such as a human, by using an ultrasound endoscope. This endoscope system 1 includes, as illustrated in FIG. 1, an ultrasound endoscope 2, an ultrasound observation device 3, an endoscope inspection device 4, and a display device 5.

The ultrasound endoscope 2 has a function as an endoscope according to the present disclosure. This ultrasound endoscope 2 is structured such that a part thereof can be inserted into the body of a subject, and has a function of transmitting ultrasonic pulses toward a body wall in the subject and receiving an ultrasonic echo reflected by the subject, a function of outputting an echo signal, and a function of imaging inside the subject and outputting an image signal.

The detailed structure of the ultrasound endoscope 2 is explained later.

The ultrasound observation device 3 is electrically connected to the ultrasound endoscope 2 through an ultrasound cable 31 (FIG. 1), outputs a pulse signal to the ultrasound endoscope 2 through the ultrasound cable 31, and receives an echo signal input from the ultrasound endoscope 2. The ultrasound observation device 3 subjects the echo signal to predetermined processing to generate an ultrasonic image.

To the endoscope inspection device 4, an endoscope connector 24 (FIG. 1) described later of the ultrasound endoscope 2 is detachably connected. This endoscope inspection device 4 includes, as illustrated in FIG. 1, a video processor 41 and a light source device 42.

The video processor 41 receives an image signal input from the ultrasound endoscope 2 through the endoscope connector 24. The video processor 41 subjects the image signal to predetermined processing to generate an endoscopic image.

The light source device 42 supplies illumination light to illuminate inside the subject through the endoscope connector 24.

The display device 5 is structured by using a liquid crystal or an organic electroluminescence (EL), and displays an ultrasound image generated by the ultrasound observation device 3, or an endoscopic image generated by the endoscope inspection device 4.

Structure of Ultrasound Endoscope

The ultrasound endoscope 2 includes, as illustrated in FIG. 1, an insertion portion 21, an operating portion 22, a universal cable 23, and the endoscope connector 24.

"Distal end side" described in the following signifies a distal end side of the insertion portion 21 (distal end side of an insertion direction into a subject). Furthermore, "proximal end side" described in the following signifies a side distant from a distal end of the insertion portion 21.

The insertion portion 21 is a portion to be inserted in the subject. This insertion portion 21 includes, as illustrated in FIG. 1, an ultrasound probe 211 that is arranged on a distal end side, a hard member 212 that is provided on the proximal end side of the ultrasound probe 211 in a continuous manner, a bending portion 213 that is bendable and connected to a proximal end side of the hard member 212, and a flexible tube 214 that is connected to a proximal end side of the bending portion 213 and that has flexibility.

In the insertion portion 21, the operating portion 22, the universal cable 23, and the endoscope connector 24, a light guide (not illustrated) that transmits illumination light supplied by the light source device 42 and plural signal cables (not illustrated) that transmit the pulse signal, the echo signal, and the image signal described above are routed.

In the following, structures of the ultrasound probe 211 and the hard member 212 out of the respective components 211 to 214 constituting the insertion portion 21 are explained.

The ultrasound probe 211 is a convex ultrasound probe, and has multiple ultrasound transducers (not illustrated) that are regularly arranged to form a convex conical shape. As the ultrasound probe 211, not limited to the convex ultrasound probe, a radial ultrasound probe can be adopted.

The ultrasound transducer has an acoustic lens, a piezoelectric device, and a matching layer, and acquires an ultrasound echo that contributes to an ultrasound tomographic image of an inside of a body wall of a subject.

The ultrasound probe 211 converts a pulse signal input from the ultrasound observation device 3 through the signal cable (not illustrated) described above into an ultrasonic pulse to transmit into the subject. Moreover, the ultrasound probe 211 converts an ultrasound echo reflected from the inside of the subject into an electrical echo signal to output to the ultrasound observation device 3 through the signal cable (not illustrated) described above.

The hard member 212 is a hard member that is made from a resin material or the like, and has a substantially pillar shape that extends along the insertion direction of the insertion portion 21. In the hard member 212, An illumination hole (not illustrated) that penetrate through from the proximal end to the distal end, respectively, an imaging hole (not illustrated), a treatment tool channel 2121, an air/water supply hole 2122, a water supply hole 2123, and a suction hole 2124 are formed (refer to FIG. 2).

Inside the illumination hole (not illustrated), an emitting end side of the light guide (not illustrated) described above is inserted. The illumination light provided from the light source device 42 is irradiated to the inside of the subject through the illumination hole.

In the imaging hole (not illustrated), an objective optical system (not illustrated) that converges light (a subject image) reflected inside the subject, and an imaging device (not illustrated) that images the subject image converged by the objective optical system are arranged. An image signal obtained by imaging by the imaging device is transmitted to the endoscope inspection device 4 (video processor 41) through the signal cable (not illustrated) described above.

The treatment tool channel 2121 is a hole to make a treatment tool (for example, a puncture needle) inserted to the inside (a first tube 61 on a distal end side described later) of the insertion portion 21 protrude outside, and is a hole to suck fluid inside the subject.

The air/water supply hole 2122 is a hole to supply air or water to the imaging hole (not illustrated) described above, and to clean the objective optical system (not illustrated).

The water supply hole 2123 is a hole to fill water in a balloon (not illustrated) that is attached to the distal end of the insertion portion 21 to cover the ultrasound probe 211.

The suction hole 2124 is a hole to suck water inside the balloon (not illustrated).

The operating portion 22 is a portion that is connected to the proximal end side of the insertion portion 21, and that receives various kinds of operation from a doctor or the like. The operating portion 22 includes, as illustrated in FIG. 1, a bending knob 221 to bend the bending portion 213, and operating members 222 to perform various kinds of operation.

In the insertion portion 21 and the operating portion 22, distal-end-side first to fifth tubes 61 to 65 (refer to FIG. 2) are provided. Moreover, in the operating portion 22, an air/water supply cylinder 7 and a suction cylinder 8 (refer to FIG. 2) that communicate with the distal-end-side first to fifth tubes 61 to 65 are provided. Furthermore, in the air/water supply cylinder 7 and the suction cylinder 8, an air/water supply button 11 (refer to FIG. 4, FIG. 5) and a suction button 14 (refer to FIG. 7 to FIG. 9) that constitute part of the operating members 222 and that switch the connection state of the distal-end-side first to fifth tubes 61 to 65 and the proximal-end-side first to third tubes 66 to 68 (refer to FIG. 2) described later according to an operation by a doctor or the like are provided, respectively.

The distal-end-side first to fifth tubes 61 to 65 and the proximal-end-side first to third tubes 66 to 68 correspond to a plurality of tubes 6 (refer to FIG. 6) according to the present disclosure. Moreover, the air/water supply button 11 and the suction button 14 correspond to an endoscope button 10 (refer to FIG. 4, FIG. 5, FIG. 7 to FIG. 9) according to the present disclosure. The detailed structures of the tubes 6, the air/water supply cylinder 7, the suction cylinder 8, and the endoscope button 10 are described later.

The universal cable 23 extends from the operating portion 22, and is a cable in which the light guide (not illustrated) and the signal cables (not illustrated) are arranged.

The endoscope connector 24 is arranged at an end portion of the universal cable 23. The endoscope connector 24 is inserted into an ultrasound connector 241 (FIG. 1) to which the ultrasound cable 31 is connected, and into the endoscope inspection device 4, and includes a plug portion 242 (refer to FIG. 2) that is connected to the video processor 41 and the light source device 42.

In the operating portion 22, the universal cable 23, and the endoscope connector 24, the proximal-end-side first to third tubes 66 to 68 (refer to FIG. 2) that communicate with the air/water supply cylinder 7 and the suction cylinder 8 arranged in the operating portion 22 are provided.

Moreover, in the plug portion 242, multiple electric contacts (not illustrated), a light-guide fitting part 243 (refer to FIG. 2), and an air-supply fitting part 244 (refer to FIG. 2) are arranged.

The multiple electric contacts are portions that electrically connect the video processor 41 when the endoscope connector 24 is inserted in the endoscope inspection device 4.

The light-guide fitting part 243 is a part to which an emitting end side of the light guide (not illustrated) described above is inserted, and that optically connects the light guide and the light source device 42 when the endoscope connector 24 is inserted in the endoscope inspection device 4.

The air-supply fitting part 244 is a part that connects to a light source pump P1 (refer to FIG. 2) provided inside the light source device 42 when the endoscope connector 24 is inserted in the endoscope inspection device 4.

Furthermore, in the endoscope connector 24, first and second water-supply fitting parts 245, 246 (refer to FIG. 2) to which an outside water supply tank Ta (refer to FIG. 2) is respectively connected, and a suction fitting part 247 (refer to FIG. 2) to which an external suction pump P2 (refer to FIG. 2) is connected are provided.

Structure of Tubes

Figure 2:
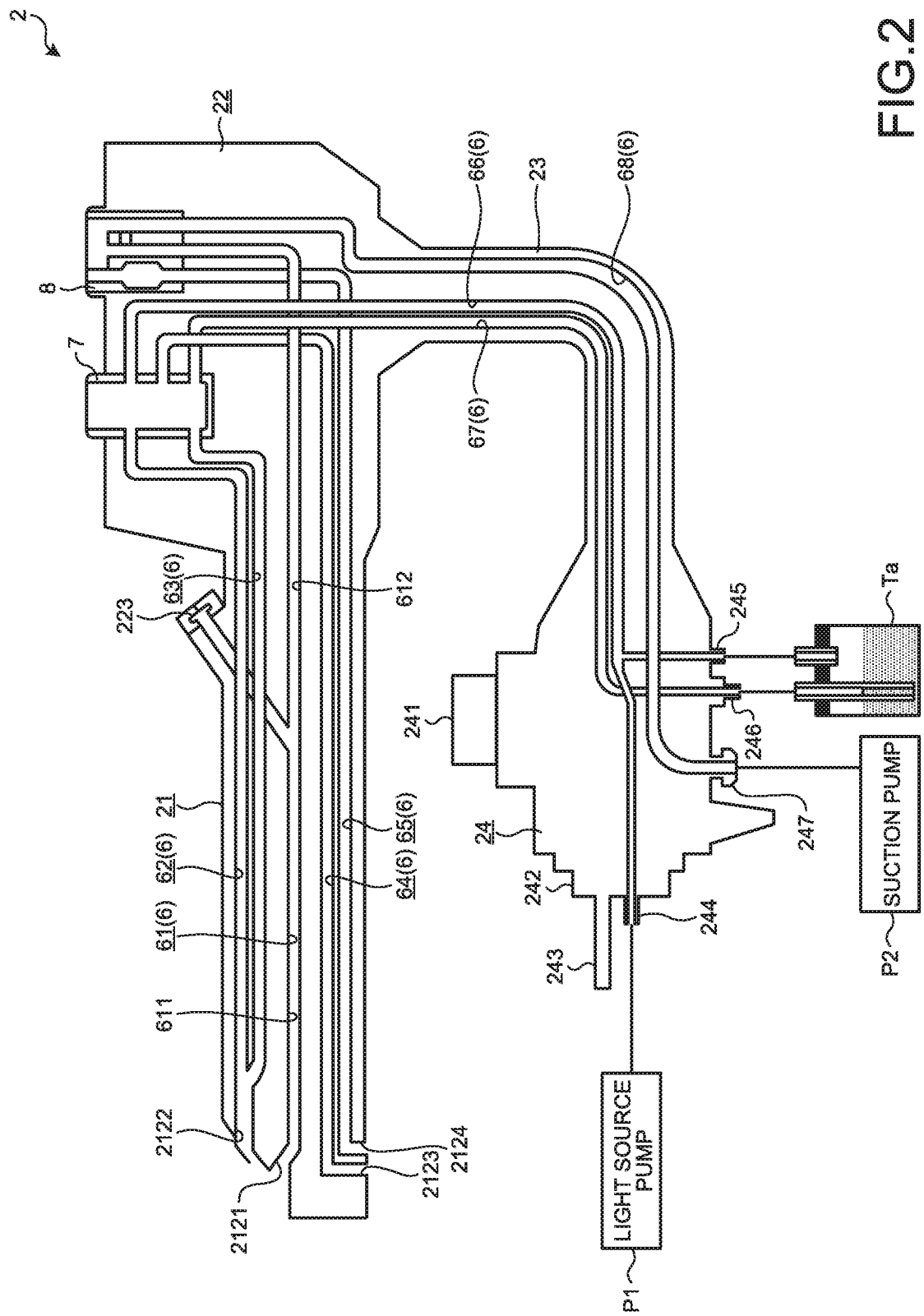
FIG. 2 is a schematic diagram of plural tubes provided in an ultrasound endoscope.

FIG. 2 is a schematic diagram of the plural tubes 6 provided in the ultrasound endoscope 2.

In the following, the plural tubes 6 are explained, referring to FIG. 2.

The plural tubes 6 are constituted of the distal-end-side first to fifth tubes 61 to 65 and the proximal-end-side first to third tubes 66 to 68 as described above.

The distal-end-side first tube 61 is a tube to let a treatment tool (for example, a puncture needle and the like) protrude outside from the treatment tool channel 2121, and is a tube to suck fluid in the subject from the treatment tool channel 2121. This distal-end-side first tube 61 includes, as illustrated in FIG. 2, a treatment tool tube 611 and a suction tube 612.

The treatment tool tube 611 is routed inside the bending portion 213 and the flexible tube 214, and communicates with the treatment tool channel 2121 at one end. Moreover, the treatment tool tube 611 communicates with a treatment-tool insertion inlet 223 (FIG. 1, FIG. 2) arranged in the operating portion 22. That is, a treatment tool (for example, a puncture needle, and the like) is inserted in the treatment tool tube 611 through the treatment-tool insertion inlet 223, and protrudes out from the treatment tool channel 2121.

The suction tube 612 is routed inside the operating portion 22, and communicates with the other end of the treatment tool tube 611 at one end, and with the suction cylinder 8 at the other end.

The distal-end-side second tube 62 is a tube to supply air to the imaging hole (not illustrated) from the air/water supply hole 2122, routed in the bending portion 213, the flexible tube 214, and the operating portion 22, and communicates with the air/water supply hole 2122 at one end and with the air/water supply cylinder 7 at the other end.

The distal-end-side third tube 63 is a tube to supply water to the imaging hole (not illustrated) from the air/water supply hole 2122, routed in the bending portion 213, the flexible tube 214, and the operating portion 22, and communicates with the air/water supply hole 2122 at one end and with the air/water supply cylinder 7 at the other end.

The distal-end-side fourth tube 64 is a tube to fill water in a balloon (not illustrated) from the water supply hole 2123, routed in the bending portion 213, the flexible tube 214, and the operating portion 22, and communicates with the water supply hole 2123 at one end and with the air/water supply cylinder 7 at the other end.

The distal-end-side fifth tube 65 is a tube to suck water in the balloon out from the suction hole 2124 (not illustrated), routed in the bending portion 213, the flexible tube 214, and the operating portion 22, and communicates with the suction hole 2124 at one end and with the suction cylinder 8 at the other end.

The proximal-end-side first tube 66 is a tube to let air ejected from the light source pump P1 flow to the air/water supply cylinder 7 and the water supply tank Ta, and is routed in the operating portion 22, the universal cable 23, and the endoscope connector 24. The proximal-end-side first tube 66 has two branches that respectively communicate with the air-supply fitting part 244 and the first water-supply fitting part 245 at respective ends, and communicates with the air/water supply cylinder 7 at the other end.

The proximal-end-side second tube 67 is a tube to let water ejected from the water supply tank Ta flow to the proximal-end-side first tube, and is routed in the operating portion 22, the universal cable 23, and the endoscope connector 24. The proximal-end-side second tube 67 communicates with the second water-supply fitting part 246 at one end, and with the air/water supply cylinder 7 at the other end.

The proximal-end-side third tube 68 is a tube to suck out fluid in the suction cylinder 8, routed in the operating portion 22, the universal cable 23, and the endoscope connector 24, and communicates with the suction fitting part 247 at one end, and with the suction cylinder 8 at the other end.

Structure of Air/Water Supply Cylinder

Figure 3:
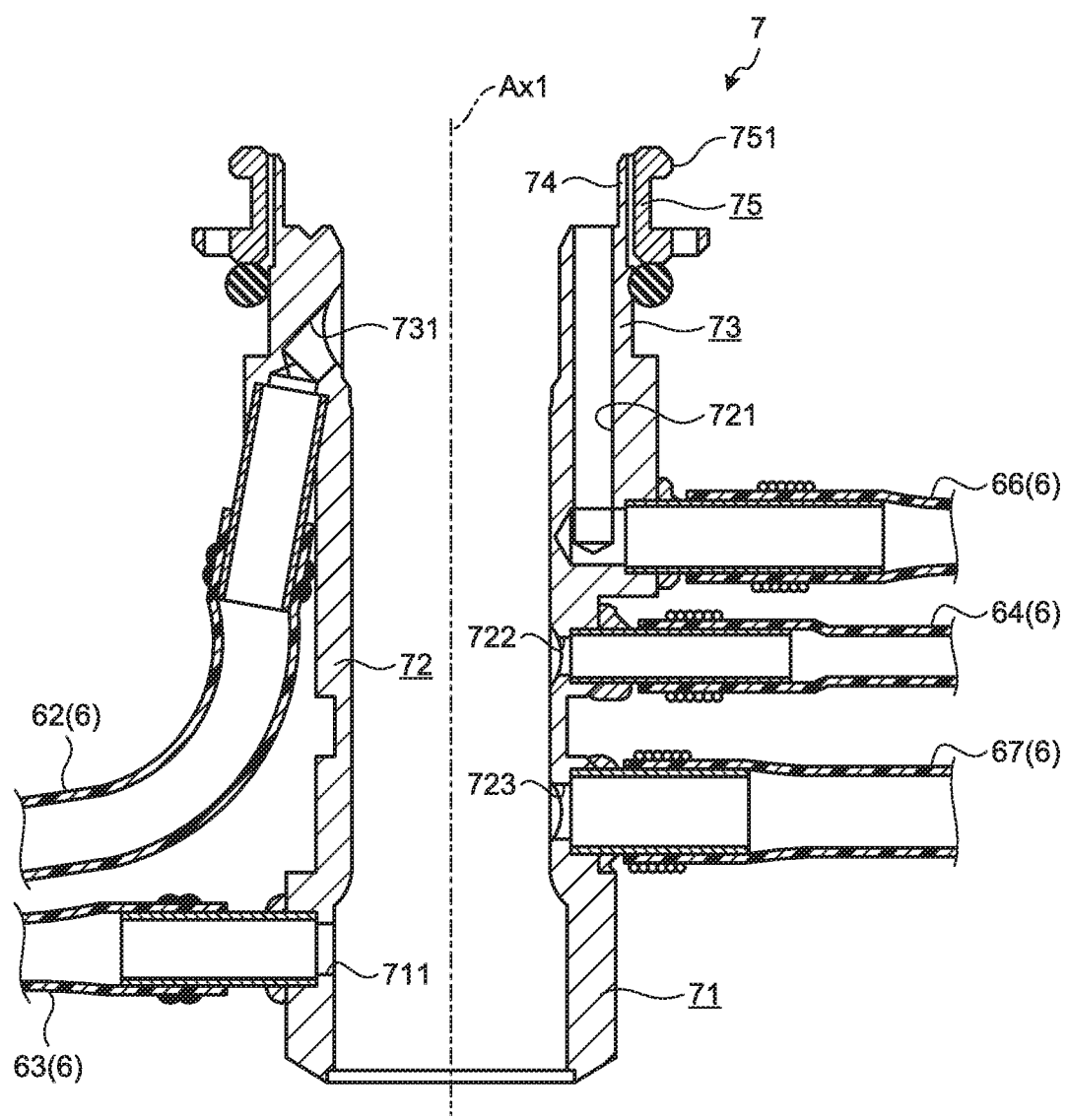
FIG. 3 is a cross-section illustrating a structure of an air/water supply cylinder.

FIG. 3 is a cross-section illustrating a structure of the air/water supply cylinder 7.

In the following, a structure of the air/water supply cylinder 7 is explained, referring to FIG. 3.

The air/water supply cylinder 7 has a bottomed cylindrical shape with having an axis Ax1 extending in the vertical direction as a center axis in FIG. 3. The air/water supply cylinder 7 has a structure in which a lower-end cylinder portion 71, a sliding cylinder portion 72, an upper-end cylinder portion 73, and an fitting cylinder portion 74 are arranged in series along the center axis Ax1 sequentially from the lower side (a bottom side of the air/water supply cylinder 7 in the bottomed cylindrical shape) to the upper side (an opening side of the air/water supply cylinder 7 in the bottomed cylindrical shape) as illustrated in FIG. 3.

In a side wall of the lower-end cylinder portion 71, a communication path 711 that communicates between the inside and the outside of the lower-end cylinder portion 71 is formed. In the communication path 711, the other end of the distal-end-side third tube 63 is connected through fittings or the like as illustrated in FIG. 3.

The sliding cylinder portion 72 has a smaller inner diameter than an inner diameter of the lower-end cylinder portion 71. In a side wall of this sliding cylinder portion 72, communication paths 721 to 723 that communicate between the inside and the outside of the air/water supply cylinder 7 are formed sequentially from the upper side to the lower side as illustrated in FIG. 3. To the communication path 721, the other end of the proximal-end-side first tube 66 is connected through fittings or the like. Moreover, to the communication path 722, the other end of the distal-end-side fourth tube 64 is connected through fittings or the like. Furthermore, to the communication path 723, the other end of the proximal-end-side second tube 67 is connected through fittings or the like.

The communication path 721 is bent inside the side wall of the sliding cylinder portion 72 upward, and opens on an upper side surface of the upper-end cylinder portion 3.

The upper-end cylinder portion 73 has a larger inner diameter than the inner diameter of the sliding cylinder portion. In a side wall of the upper-end cylinder portion 73, a communication path 731 that communicates between the inside and the outside of the upper-end cylinder portion 73 is formed as illustrated in FIG. 3. To the communication path 731, the other end of the distal-end-side second tube 62 is connected.

The fitting cylinder portion 74 has a larger inner diameter than the inner diameter of the upper-end cylinder portion 73. On an outer peripheral surface of the fitting cylinder portion 74, a fitting part 75 to mount the air/water supply button 11 is fixed as illustrated in FIG. 3.

This fitting part 75 has a cylindrical shape, and is fixed on the outer peripheral surface of the fitting cylinder portion 74, for example, by screwing. The fitting part 75 protrudes to the outside from the inside of the operating portion 22, fixed to the outer peripheral surface of the fitting cylinder portion 74.

On an outer peripheral surface of this fitting part 75, an engagement protruding portion 751 that has a ring shape extending all around the entire perimeter of the outer peripheral surface and that protrudes toward a direction apart from the center axis Ax1 from an upper end of the outer peripheral surface is arranged as illustrated in FIG. 3.

Structure of Air/Water Supply Button

Figure 4:
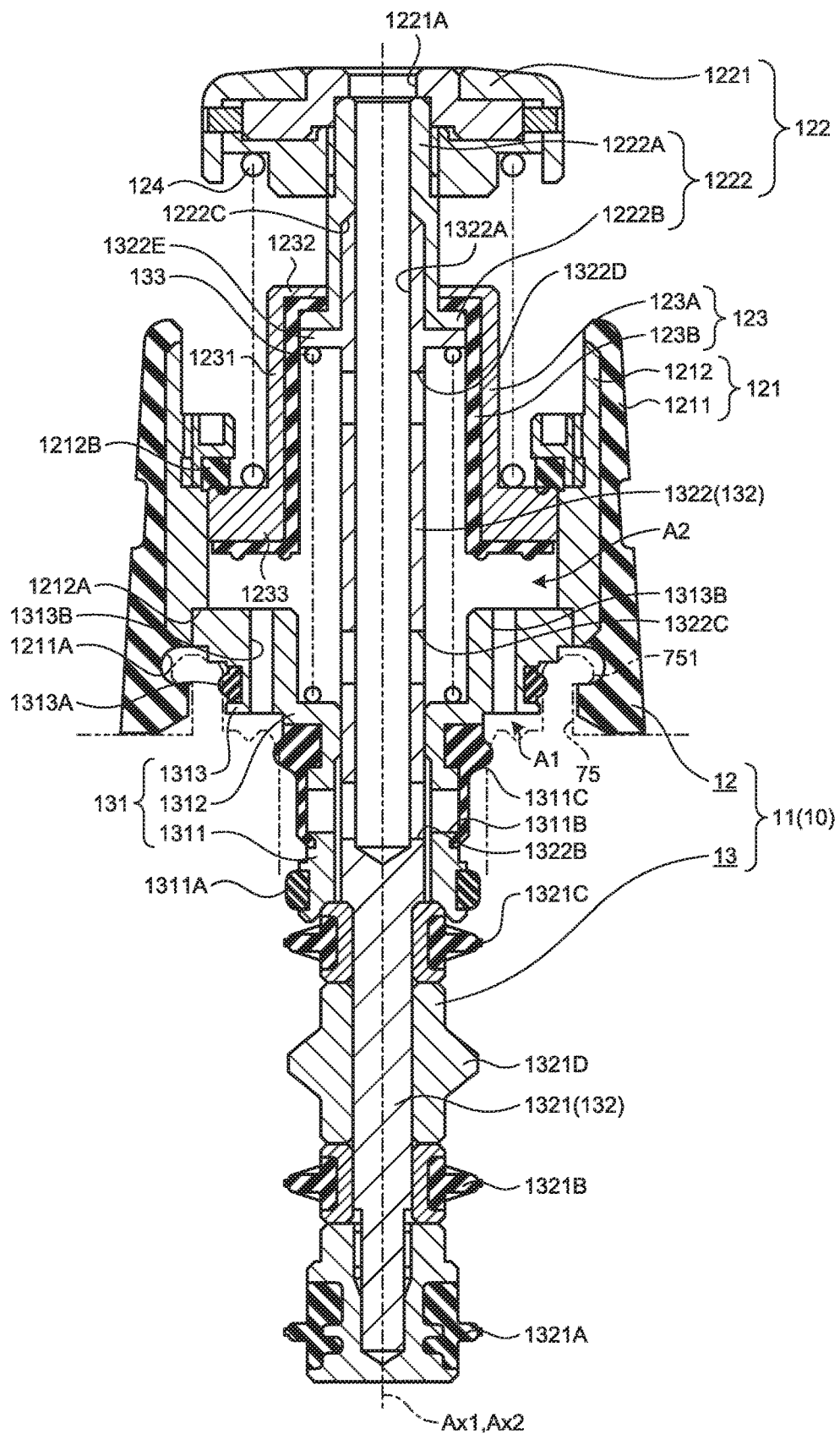
FIG. 4 illustrates a structure of an air/water supply button.
Figure 5:
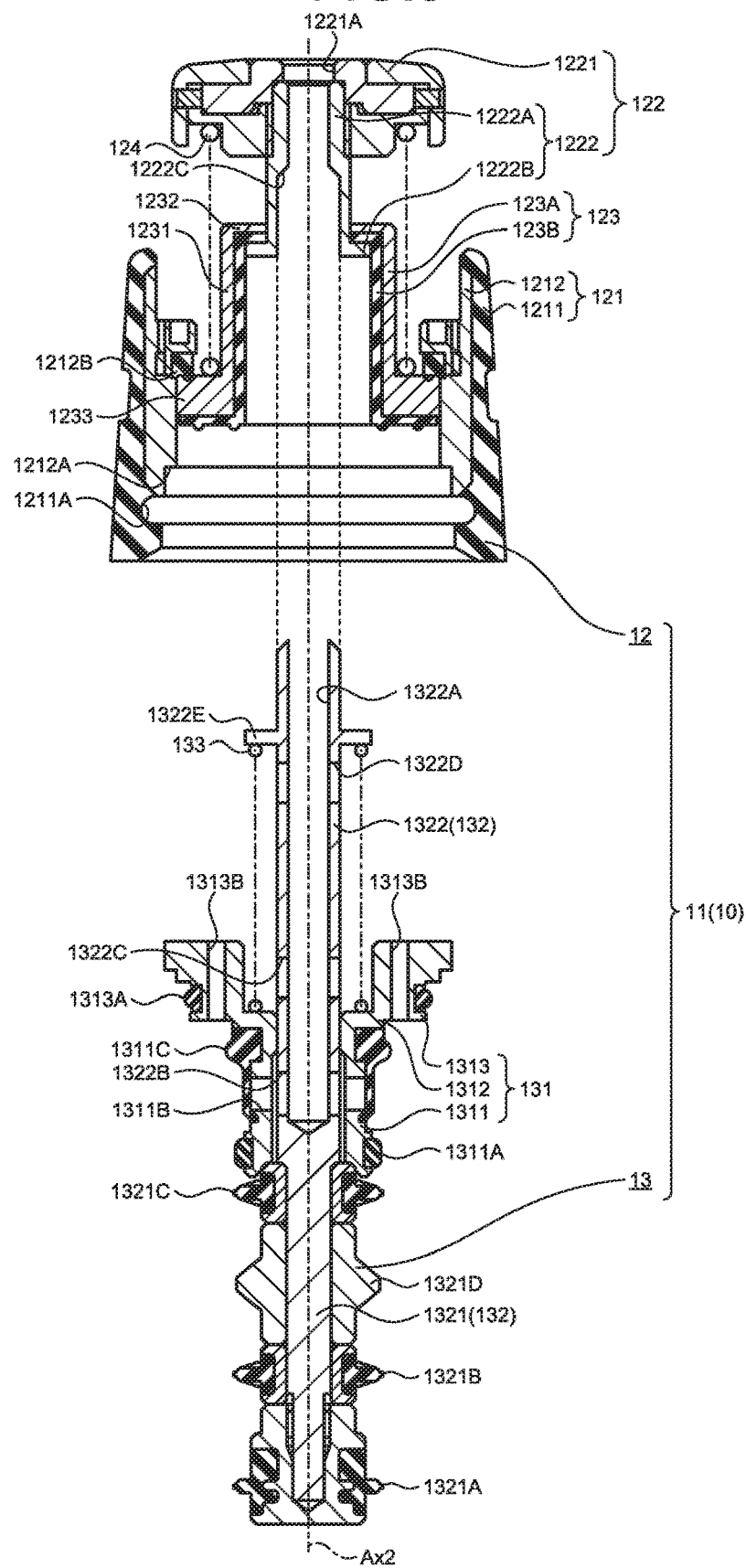
FIG. 5 illustrates a structure of the air/water supply button.

FIG. 4 and FIG. 5 illustrate a structure of the air/water supply button 11. Specifically, FIG. 4 is a cross-section showing a state in which the air/water supply button 11 is mounted on the fitting part 75 (the air/water supply cylinder 7). That is, the lower side in FIG. 4 is the distal end side in a mounting direction of the air/water supply button 11. FIG. 5 is a cross-section showing a state in which the air/water supply button 11 is removed from the fitting part 75 (the air/water supply cylinder 7). In FIG. 5, the lower side is the same direction (the distal end side in the mounting direction) as the lower side in FIG. 4.

In the following, the structure of the air/water supply button 11 is explained, referring to FIG. 4 and FIG. 5.

The air/water supply button 11 includes air/water supply first and second units 12, 13 that are integrated when attached to the fitting part 75 (the air/water supply cylinder 7) (FIG. 4), and that are separated from each other when removed (FIG. 5) from the fitting part 75 (the air/water supply cylinder 7).

Structure of Air/Water Supply First Unit

The air/water supply first unit 12 functions as a first unit according to the present disclosure. This air/water supply first unit 12 includes, as illustrated in FIG. 4 or FIG. 5, a cylindrical member 121, a pressing member 122, a second movable member 123, and an outside spring member 124.

The cylindrical member 121 has an overall substantially cylindrical shape having an axis Ax2 extending in the vertical direction in FIG. 4 or FIG. 5 as the center axis. This cylindrical member 121 has a structure in which an outer-periphery rubber cylinder 1211 and an inner-periphery metal cylinder 1212 are joined into one piece as illustrated in FIG. 4 or FIG. 5.

On an inner peripheral surface of the rubber cylinder 1211, an engagement concave portion 1211A that has a ring shape extending all around the entire perimeter of the inner peripheral surface, and to which the engagement protruding portion 751 is inserted is formed as illustrated in FIG. 4 or FIG. 5. By hooking the engagement protruding portion 751 on the engagement concave portion 1211A, the air/water supply button 11 is attached to the fitting part 75 (the air/water supply cylinder 7 (FIG. 4). In this state, the center axis Ax1 of the air/water supply cylinder 7 and the center axis Ax2 of the cylindrical member 121 (the air/water supply button 11) are coaxial.

The metal cylinder 1212 is arranged above the engagement concave portion 1211A on an inner peripheral surface of the rubber cylinder 1211.

On an inner periphery side at a lower end of this metal cylinder 1212, a ring-shaped concave portion 1212A that recesses from the lower end toward the upper side, and that extends all around the entire perimeter of an inner peripheral surface of the metal cylinder 1212 is formed as illustrated in FIG. 4 or FIG. 5.

The concave portion 1212A functions as an engaging unit.

Moreover, on the inner peripheral surface of the metal cylinder 1212, a gasket member 1212B having a ring shape is fixed, for example, by screwing as illustrated in FIG. 4 or FIG. 5.

The pressing member 122 is a part receiving a depression operation (air/water supply operation) by a doctor or the like. This pressing member 122 includes, as illustrated in FIG. 4 or FIG. 5, a pressing member body 1221 and an axis member 1222.

The pressing member body 1221 is a part that accepts an air/water supply operation by a doctor or the like, and is formed in a substantially cylindrical shape coaxial with the cylindrical member 121, and has a smaller inner diameter than the cylindrical member 121 and a larger outer diameter than an inner diameter of the gasket member 1212B.

In this pressing member body 1221, a leak hole 1221A that penetrates through top and bottom surfaces and that has a substantially circular shape when viewed from top is formed on the center axis Ax2.

The axis member 1222 includes, as illustrated in FIG. 4 or FIG. 5, an axis member body 1222A and a jut-out portion 1222B.

The axis member body 1222A has a cylindrical shape coaxial with the cylindrical member 121, communicates with the leak hole 1221A at the inside, and is fixed to the pressing member body 1221, protruding out toward the lower side of the pressing member body 1221. This axis member body 1222A has an inner peripheral surface that is arranged such that an inner diameter is larger at an upper portion and smaller at a lower portion as illustrated in FIG. 4 or FIG. 5, and is formed in a stepped shape having a step portion 1222C.

The jut-out portion 1222B has a ring shape extending all around the entire perimeter of an outer peripheral surface of the axis member body 1222A, and juts out from a lower end of the outer peripheral surface toward a direction opposite to the center axis Ax2.

The second movable member 123 has an overall substantially cylindrical shape coaxial with the cylindrical member 121. This second movable member 123 has a structure in which a metal hat 123A on an outer periphery side and a rubber hat 123B on an inner periphery side are joined into one piece as illustrated in FIG. 4 or FIG. 5, and includes a cylinder portion 1231, an inward jut-out portion 1232, and an outward jut-out portion 1233.

The cylinder portion 1231 is a cylindrical part coaxial with the cylindrical member 121, and has an inner diameter a little larger than an outer diameter of the jut-out portion 1222B, and has a smaller outer diameter than an inner diameter of the cylindrical member 121.

The inward jut-out portion 1232 is a ring-shaped part that juts out toward the center axis Ax2 from an upper end of the cylinder portion 1231, and has an inner diameter a little larger than an outer diameter of the axis member body 1222A.

The pressing member 122 is installed to be movable along the center axis Ax2 with respect to the second movable member 123.

Specifically, the pressing member 122 is structured such that a lower portion of the axis member body 1222A is positioned inside the cylinder portion 1231, and to be movable along the center axis Ax2 while an external peripheral surface of the jut-out portion 1222B slides on an inner peripheral surface (the rubber hat 123B) of the cylinder portion 1231. At this time, the pressing member body 1221 and the inward jut-out portion 1232 abut against each other when the pressing member 122 moves downward with respect to the second movable member 123, to prevent the pressing member 122 from falling off from the second movable member 123. Moreover, the jut-out portion 1222B and the inward jut-out portion 1232 abut against each other when the pressing member 122 moves upward with respect to the second movable member 123, to prevent the pressing member from popping off from the second movable member 123.

The outward jut-out portion 1233 is a ring-shaped part that juts out toward a direction opposite to the center axis Ax2 from a lower end of the cylinder portion 1231, and has an outer diameter a little smaller than an inner diameter of the cylindrical member 121 (the metal cylinder 1212).

The second movable member 123 is installed to be movable with respect to the cylindrical member 121 along the center axis Ax2.

Specifically, the second movable member 123 is arranged to be movable along the center axis Ax2 while an outer peripheral surface of the outward jut-out portion 1233 slides on an inner peripheral surface of the cylindrical member 121 (the metal cylinder 1212). At this time, the gasket member 1212B and the pressing member body 1221 abuts against each other when the second movable member 123 moves downward with respect to the cylindrical member 121, to prevent the second movable member 123 from falling off from the cylindrical member 121. Moreover, the gasket member 1212B and the outward jut-out portion 1233 abuts against each other when the second movable member 123 moves upward with respect to the cylindrical member 121, to prevent the second movable member 123 from popping off from the cylindrical member 121.

The outside spring member 124 is constituted of a compression coil spring, and is positioned inside the cylinder portion 1231, abutting on a lower surface of the pressing member body 1221 at one end, and abutting against an upper surface of the outward jut-out portion 1233 at the other end. The outside spring member 124 applies a pushing force to make the pressing member 122 and the second movable member 123 move apart from each other along the center axis Ax2.

Structure of Air/Water Supply Second Unit

The air/water supply second unit 13 functions as a second unit according to the present disclosure. This air/water supply second unit 13 includes, as illustrated in FIG. 4 or FIG. 5, a fixing member 131, a first movable member 132, and an inside spring member 133.

The fixing member 131 is inserted inside the cylindrical member 121 in a state in which the air/water supply button 11 is attached to the fitting part 75 (in a state in which the air/water supply first and second units 12, 13 are joined with each other into one piece), and is fixed with respect to the inner peripheral surface of the cylindrical member 121. This fixing member 131 is formed in an overall substantially cylindrical shape coaxial with the cylindrical member 121, and has a structure in which a small diameter portion 1311, a flange portion 1312, and a large diameter portion 1313 are arranged in series sequentially from the lower side toward the upper side.

The small diameter portion 1311 is a part fit inside the upper-end cylinder portion 73 and the sliding cylinder portion 72 of the air/water supply cylinder 7 in a state in which the air/water supply button 11 is attached to the fitting part 75. This small diameter portion 1311 has substantially the same diameter as the inner diameter of a lower portion of the axis member body 1222A.

In the lower portion of this small diameter portion 1311, an O-ring gasket 1311A is attached as illustrated in FIG. 4 or FIG. 5. In a state in which the air/water supply button 11 is attached to the fitting part 75, the gasket 1311A abuts on an inner peripheral surface of the sliding cylinder portion 72. Thus, an interior portion of the air/water supply button 11 and an interior portion of the upper-end cylinder portion 73 are separated in a watertight and airtight manner.

Furthermore, in a side wall of the small diameter portion 1311, plural communication holes 1311B that communicates between the inside and the outside thereof are formed at predetermined intervals around the center axis Ax2 as illustrated in FIG. 4 or FIG. 5. Moreover, on an outer peripheral surface of the small diameter portion 1311, a check valve 1311C in a ring shape extending all around the entire perimeter of the outer peripheral surface to cover the communication holes 1311B is attached. An upper end portion of the check valve 1311C abuts against an inner peripheral surface of the upper-end cylinder portion 73 in a state in which the air/water supply button 11 is attached to the fitting part 75. Thus, an interior portion of the upper-end cylinder portion 73 and an interior portion of the fitting cylinder portion 74 are separated in a watertight and airtight manner.

The flange portion 1312 has a ring shape that protrudes out to a direction opposite to the center axis Ax2 from an upper end of the small diameter portion 1311.

The large diameter portion 1313 is formed in one piece with the flange portion 1312, connecting an inner peripheral region of a lower end with an outer peripheral region of an upper surface of the flange portion 1312. The large diameter portion 1313 is pushed downward as the upper end abuts on (engages with) the concave portion 1212A when the cylindrical member 121 is attached to the fitting part 75. Thus, the fixing member 131 is fixed to the cylindrical member 121. The air/water supply second unit 13 is joined together with the air/water supply first unit 12 as the fixing member 131 engages with the concave portion 1212A when the cylindrical member 121 is attached to the fitting part 75. Moreover, the air/water supply second unit 13 is separated from the air/water supply first unit 12 as the engagement between the fixing member 131 and the concave portion 1212A is released when the cylindrical member 121 is removed from the fitting part 75.

In this large diameter portion 1313, an O-ring gasket 1313A is attached on an outer peripheral surface at a lower portion as illustrated in FIG. 4 or FIG. 5. When the air/water supply button 11 is attached to the fitting part 75, the gasket 1313A abuts against an inner peripheral surface of the fitting cylinder portion 74. Thus, airtightness and watertightness between the air/water supply button 11 and the air/water supply cylinder 7 is obtained.

Furthermore, when the air/water supply button 11 is attached to the fitting part 75, space (hereinafter, a first space A1 (FIG. 4)) is formed between a lower end surface of the large diameter portion 1313 and an upper end surface of the upper-end cylinder portion 73. In the large diameter portion 1313, communication holes 1313B that communicate with the first space A1 are formed at predetermined intervals around the center axis Ax2.

The first movable member 132 has an overall substantially cylindrical shape coaxial with the cylindrical member 121, and is inserted inside the fixing member 131. This first movable member 132 has a structure in which a distal-end axial portion 1321 and a proximal-end axial portion 1322 are arranged in series sequentially from the lower side to the upper side as illustrated in FIG. 4 or FIG. 5.

On an outer peripheral surface of the distal-end axial portion 1321, a first gasket 1321A, a second gasket 1321B, a communicating pivotal member 1321D, and a third gasket 1321C are fitted together sequentially from the lower side toward the upper side as illustrated in FIG. 4 or FIG. 5.

The first to the third gaskets 1321A to 1321C are members structured by connecting aa rubber member in an O-ring shape to, for example, a cylindrical metal base. In a state in which the air/water supply button 11 is attached to the fitting part 75, the first to the third gaskets 1321A to 1321C abut on an inner peripheral surface of the sliding cylinder portion 72. Thus, in the sliding cylinder portion 72, space divided by the first to the third gaskets 1321A to 1321C is separated in a watertight and airtight manner.

The communicating pivotal member 1321D is a member that pivotably supports the first movable member 132 with respect to the air/water supply cylinder 7 in a state in which the air/water supply button 11 is attached to the fitting part 75. This communicating pivotal member 1321D is arranged such that only part of the outer peripheral surface abuts on the inner peripheral surface of the sliding cylinder portion 72 although specific illustration is omitted. That is, the communicating pivotal member 1321D does not interfere flow of fluid present above and below the communicating pivotal member 1321D inside the sliding cylinder portion 72.

The proximal-end axial portion 1322 has an outer diameter that is larger than an outer diameter of the distal-end axial portion 1321 and is a little smaller than an inner diameter of the small diameter portion 1311 (the inner diameter of the lower portion of the axis member body 1222A)

In this proximal-end axial portion 1322, a bottomed axial hole 1322A that extends from an upper end toward a lower end is formed on the center axis Ax2 as illustrated in FIG. 4 or FIG. 5.

Furthermore, on a side wall of the proximal-end axial portion 1322, communication holes 1322B to 1322D that communicate with the bottomed axial hole 1322A are formed sequentially from the lower side to the upper side.

Moreover, in an outer peripheral surface of the proximal-end axial portion 1322, a jut-out portion 1322E that has a ring shape extending all around the entire perimeter of the outer peripheral surface, and that juts out toward a direction opposite to the center axis Ax2 from the outer peripheral surface is formed on an upper side of the communication hole 1322D.

The first movable member 132 is installed movably along the center axis Ax2 with respect to the fixing member 131.

Specifically, the first movable member 132 is structured to be movable along the center axis Ax2 while the external peripheral surface of the proximal-end axial portion 1322 slides on the inner peripheral surface of the small diameter portion 1311 and the flange portion 1312. At this time, the jut-out portion 1322E and the flange portion 1312 abut against each other when the first movable member 132 moves downward with respect to the fixing member 131, to prevent the first movable member 132 from falling off from the fixing member 131. Moreover, the third gasket 1321C and the small diameter portion 1311 abut against each other when the first movable member 132 moves upward with respect to the fixing member 131, to prevent the first movable member 132 from popping off from the fixing member 131.

The inside spring member 133 is constituted of a compression coil spring having a smaller pushing force than the outside spring member 124, and abuts on a lower surface of the jut-out portion 1322E at one end, and abuts on an upper surface of the flange portion 1312 at the other end in a state in which the proximal-end axial portion 1322 is positioned thereinside. The inside spring member 133 applies a pushing force to make the fixing member 131 and the first movable member 132 move apart from each other along the center axis Ax2.

In a state in which the air/water supply button 11 is attached to the fitting part 75, an upper portion of the proximal-end axial portion 1322 is inserted inside the axis member body 1222A. Moreover, an upper end the proximal-end axial portion 1322 abuts on the step portion 1222C. Furthermore, an upper surface of the jut-out portion 1322E abuts on a lower surface of the jut-out portion 1222B. That is, the first movable member 132 is structured to be movable along the center axis Ax2 with the pressing member 122, in response to a depression operation on the pressing member 122 (the pressing member body 1221).

Moreover, in a state in which the air/water supply button 11 is attached to the fitting part 75, space (hereinafter, second space A2 (FIG. 4) surrounded by the cylindrical member 121, the second movable member 123, and the fixing member 131 is to be a channel in which fluid flows. That is, in a state in which the air/water supply button 11 is removed from the fitting part 75 and the air/water supply first and second units 12, 13 are separated, part of the channel (the second space A2) is exposed to the outside as illustrated in FIG. 5.

Structure of Suction Cylinder

Figure 6:
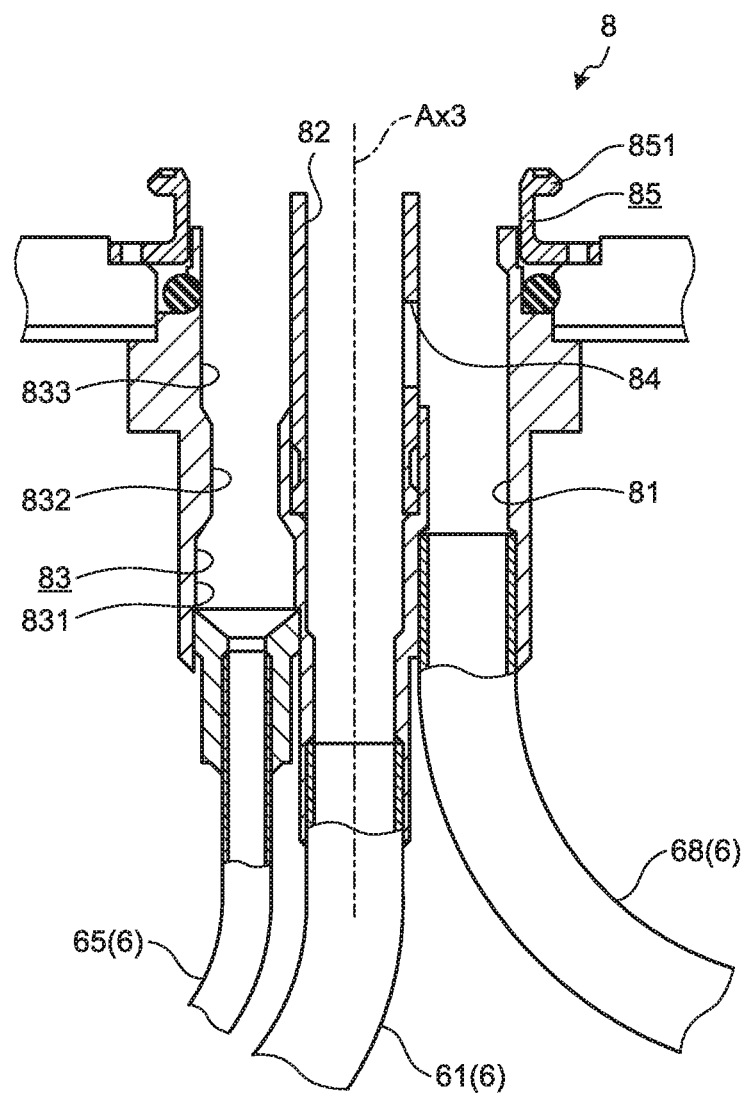
FIG. 6 is a cross-section illustrating a structure of a suction cylinder.

FIG. 6 is a cross-section illustrating a structure of the suction cylinder 8.

In the following, a structure of the suction cylinder 8 is explained, referring to FIG. 6.

The suction cylinder 8 has a bottomed cylindrical shape with an axis Ax3 extending in the vertical direction in FIG. 6 as the center axis. In the suction cylinder 8, communication channels 81 to 83 that communicate with an interior of the suction cylinder 8 and that extend from an end surface on the lower side (a bottom side of the suction cylinder 8 in a bottomed cylindrical shape) toward the upper side (an open side of the suction cylinder 8 in a bottomed cylindrical shape) are formed as illustrated in FIG. 6. To the communication channel 81, one end of the proximal-end-side third tube 68 is connected. Moreover, to the communication channel 82, the other end of the distal-end-side first tube 61 (the suction tube 612) is connected. Furthermore, to the communication channel 83, the other end of the distal-end-side fifth tube 65 is connected.

The communication channel 83 has a structure in which an expanded diameter portion 831, a small diameter portion 832 having an inner diameter smaller than the expanded diameter portion 831, and a large diameter portion 833 having an inner diameter larger than the small diameter portion 832 are arranged in series sequentially from the lower side to the upper side as illustrated in FIG. 6. Moreover, the large diameter portion 833 communicates with an upper portion of the communication channel 81.

Furthermore, in a wall between the communication channels 81, 82, a communication hole 84 that communicates between the communication channels 81, 82 is formed.

On an outer peripheral surface at an upper end of the suction cylinder 8 explained above, a fitting part 85 to attach the suction button 14 is fixed as illustrated in FIG. 6.

This fitting part 85 has a shape similar to the fitting part 75, and is fixed to the outer peripheral surface at the upper end of the suction cylinder 8, for example, by screwing. That is, the fitting part 85 has an engagement protruding portion 851 similar to the engagement protruding portion 751 in the fitting part 75.

Structure of Suction Button

Figure 7:
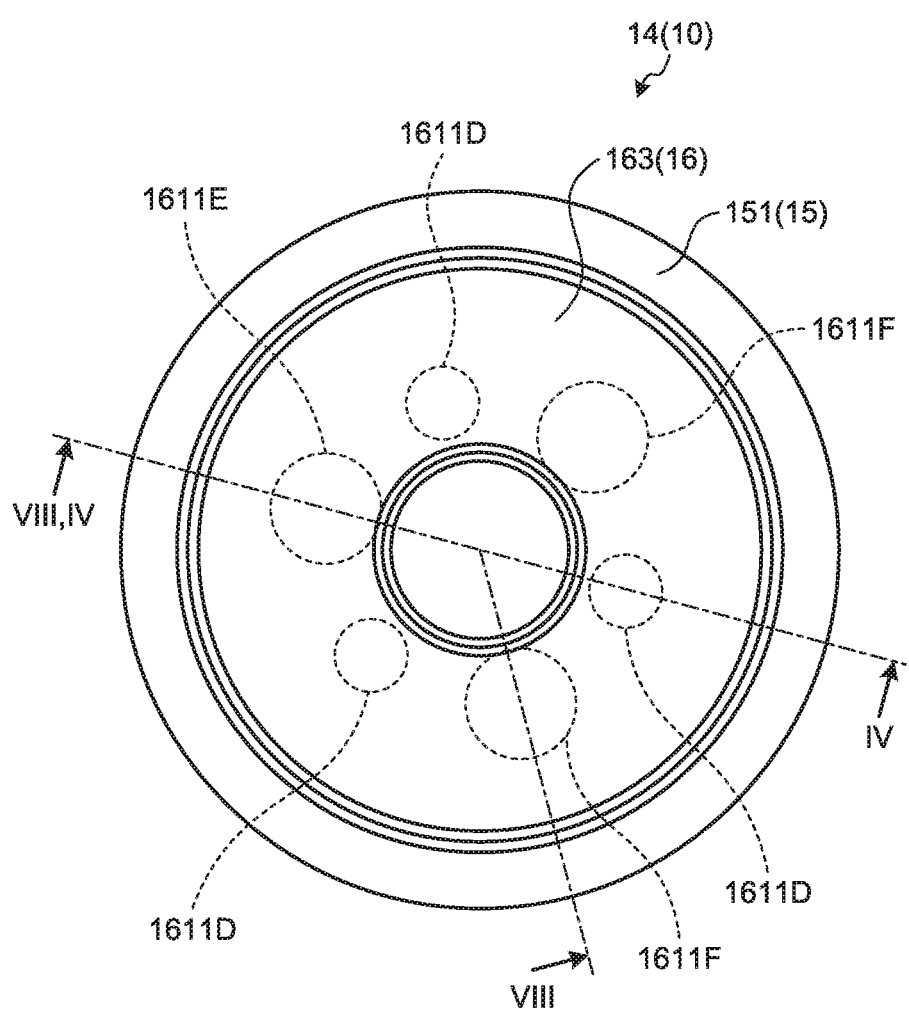
FIG. 7 illustrates a structure of a suction button.
Figure 8:
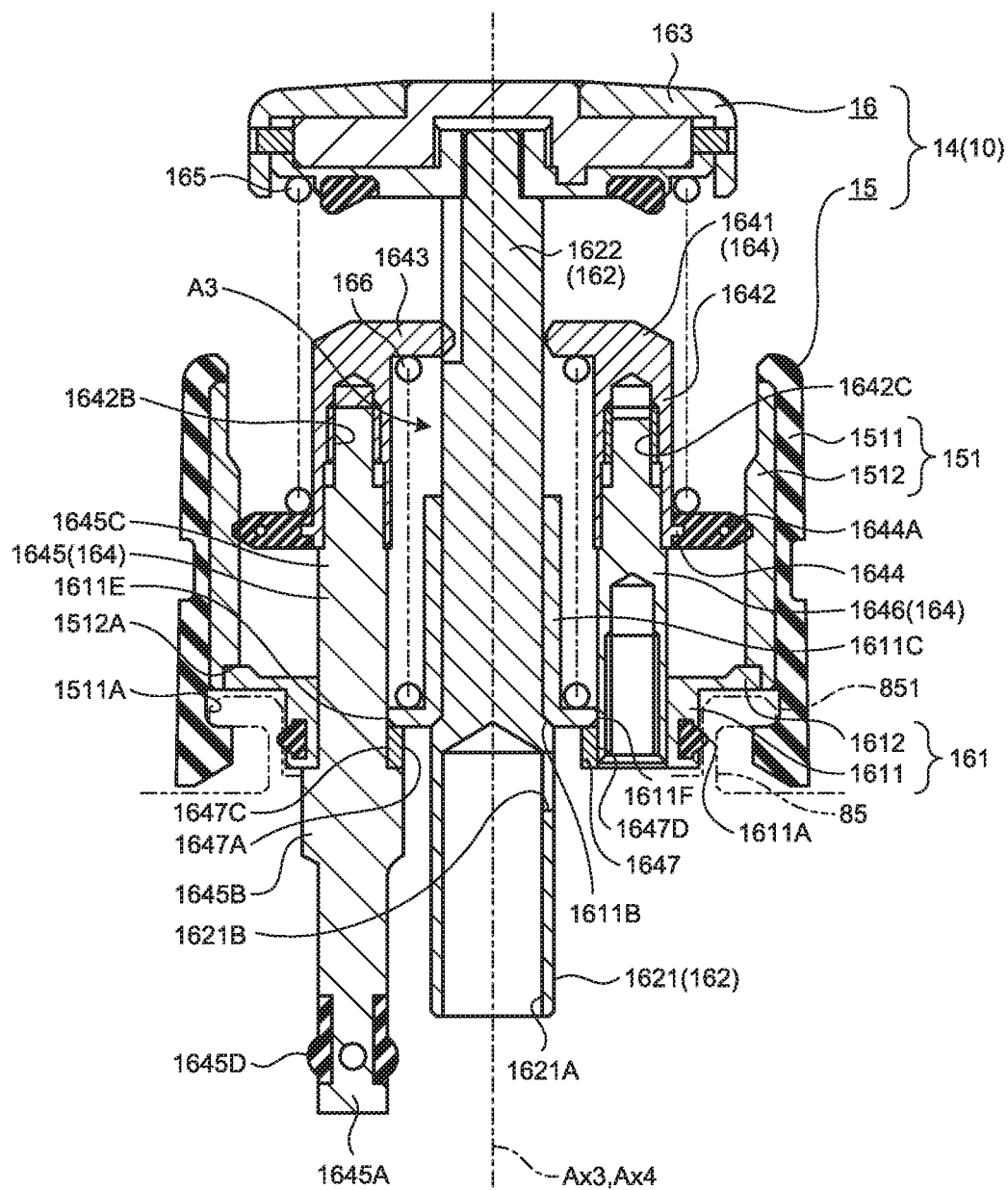
FIG. 8 illustrates a structure of the suction button.
Figure 9:
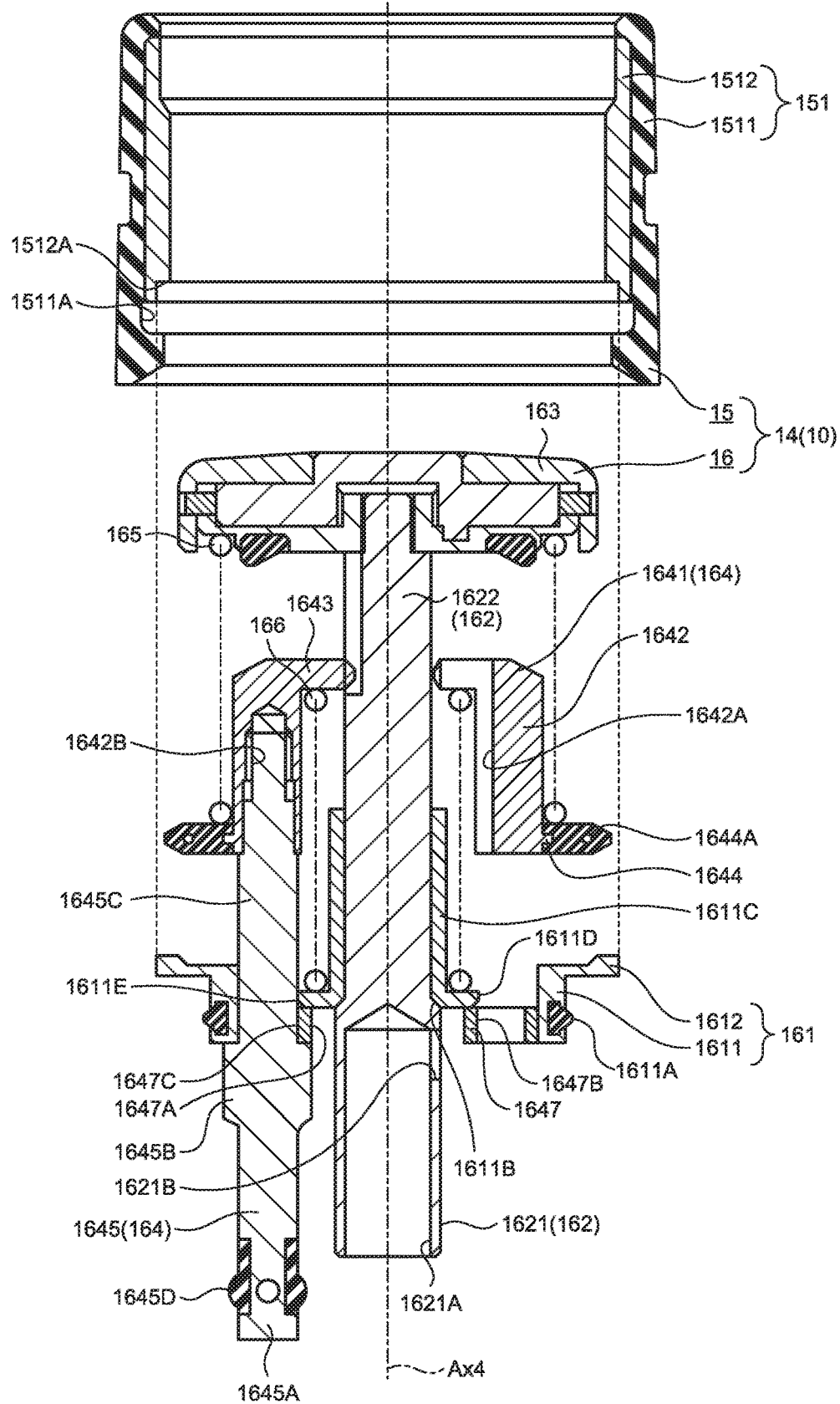
FIG. 9 illustrates a structure of the suction button.

FIG. 7 to FIG. 9 illustrate a structure of the suction button 14. Specifically, FIG. 7 shows a view of the suction button 14 from top (from a proximal end side in a mounting direction to the fitting part 85 (suction cylinder 8)). FIG. 8 shows a cross-section of the suction button 14 cut along a VIII-VIII line (a line passing through a balloon-suction insertion hole 1611E and connecting-rod insertion holes 1611F) illustrated in FIG. 7, and shows a state in which the suction button 14 is attached to the fitting part 85 (the suction cylinder 8). That is, in FIG. 8, the lower side is the distal end side in the mounting direction of the suction button 14 to the fitting part 85. FIG. 9 is a cross-section of the suction button 14 cut along a line IV-IV (a line passing through the balloon-suction insertion hole 1611E and the through hole 1611D) illustrated in FIG. 7, and shows a state in which the suction button 14 is removed from the fitting part 85 (the suction cylinder 8). In FIG. 9, the lower side is the same direction (the distal end side in the mounting direction) as the lower side in FIG. 8.

In the following, the structure of the suction button 14 is explained, referring to FIG. 7 to FIG. 9.

The suction button 14 includes suction first and second units 15, 16 that are joined together when attached to the fitting part 85 (the suction cylinder 8) (FIG. 8), and are separated from each other when removed from the fitting part 85 (the suction cylinder 8) (FIG. 9).

Structure of Suction First Unit

The suction first unit 15 functions as a first unit according to the present disclosure. This suction first unit 15 includes a cylindrical member 151 as illustrated in FIG. 8 or FIG. 9.

The cylindrical member 151 has a shape similar to the cylindrical member 121 described above. That is, the cylindrical member 151 includes, as illustrated in FIG. 8 or FIG. 9, a rubber cylinder 1511 (including an engagement concave portion 1511A) and a metal cylinder 1512 (including a concave portion 1512A) similar to the rubber cylinder 1211 (including the engagement concave portion 1211A) and the metal cylinder 1212 (including the concave portion 1212A) in the cylindrical member 121. By hooking the engagement protruding portion 851 on the engagement concave portion 1511A, the suction button 14 is attached to the fitting part 85 (the suction cylinder 8). In this state, the center axis Ax3 of the suction cylinder 8 and a center axis Ax4 of the cylindrical member 151 (the suction button 14) are coaxial.

The concave portion 1512A functions as an engaging unit according to the present disclosure.

Structure of Suction Second Unit

The suction second unit functions as a second unit according to the present disclosure. The suction second unit 16 includes, as illustrated in FIG. 8 or FIG. 9, a fixing member 161, a first movable member 162, a pressing member 163, a second movable member 164, an outside spring member 165, and an inside spring member 166.

The fixing member 161 is inserted inside the cylindrical member 151 and is fixed with respect to an inner peripheral surface of the cylindrical member 151 in a state in which the suction button 14 is attached to the fitting part 85 (in a state in which that suction first, second units 15, 16 are joined together). This fixing member 161 includes, as illustrated in FIG. 8 or FIG. 9, a fixing member body 1611 and a jut-out portion 1612.

The fixing member body 1611 is formed in a disk shape coaxial with the cylindrical member 151, and has an outer diameter a little smaller than an inner diameter of the fitting part 85.

On an outer peripheral surface of this fixing member body 1611, an O-ring gasket 1611A is attached as illustrated in FIG. 8 or FIG. 9. In a state in which the suction button 14 is attached to the fitting part 85, the gasket 1611A abuts on an inner peripheral surface of the fitting part 85. Thus, watertightness and airtightness between the suction button 14 and the suction cylinder 8 is obtained.

Moreover, in the fixing member body 1611, a through hole 1611B that penetrates through to an upper and a lower surfaces and that has a substantially circular shape when viewed from top is formed on the center axis Ax4. This through hole 1611B has an inner diameter smaller than an inner diameter of the communication channel 82. On the upper surface of the fixing member body 1611, a cylinder portion 1611C in a cylindrical shape extending upward from a rim portion of the through hole 1611B rises.

Furthermore, in the fixing member body 1611, three through holes 1611D, the balloon-suction insertion hole 1611E, and the two connecting-rod insertion holes 1611F are formed (FIG. 7 to FIG. 9).

The jut-out portion 1612 has a ring shape extending all around the entire perimeter of the outer peripheral surface of the fixing member body 1611, and juts out toward a direction opposite to the center axis Ax4 from an upper end of the outer peripheral surface. The jut-out portion 1612 is pushed downward as an outer rim portion of the upper end abuts against (engages with) the concave portion 1512A of the cylindrical member 151 when the cylindrical member 151 is attached to the fitting part 85. Thus, the fixing member 161 is fixed with respect to the cylindrical member 151. The suction second unit 16 is joined together with the suction first unit 15 as the fixing member 161 engages with the concave portion 1512A when the cylindrical member 151 when the cylindrical member 151 is attached to the fitting part 85. Moreover, the suction second unit 16 is separated from the suction first unit 15 as the engagement between the fixing member 161 and the concave portion 1512A is released when the cylindrical member 151 is removed from the fitting part 85.

The first movable member 162 has an overall substantially cylindrical shape coaxial with the cylindrical member 151, and is inserted inside the cylinder portion 1611C. This first movable member 162 has a structure in which a distal-end axial portion 1621 and a proximal-end axial portion 1622 are arranged in series sequentially from the lower side to the upper side as illustrated in FIG. 8 or FIG. 9.

The distal-end axial portion 1621 has an outer diameter a little smaller than an inner diameter of the communication channel 82 and larger than an inner diameter of the through hole 1611B.

In this distal-end axial portion 1621, a bottomed axial hole 1621A that extends from a lower end toward an upper end is formed on the center axis Ax4 as illustrated in FIG. 8 or FIG. 9.

Furthermore, on a side wall of the distal-end axial portion 1621, a communication hole 1621B that communicates with the bottomed axial hole 1621A is formed.

The proximal-end axial portion 1622 has an outer diameter that is a little smaller than the inner diameter of the through hole 1611B.

The first movable member 162 is installed movably along the center axis Ax4 with respect to the fixing member 161.

Specifically, the first movable member 162 is structured to be movable along the center axis Ax4 while an external peripheral surface of the proximal-end axial portion 1622 slides on an inner peripheral surface of the cylinder portion 1611C in a state in which the proximal-end axial portion 1622 is inserted inside the cylinder portion 1611C. At this time, the pressing member 163 and the second movable member 164 (an airtight hat 164 described later) abut against each other when the first movable member 162 moves downward with respect to the fixing member 161, to prevent the first movable member 162 from falling off from the fixing member 161. Moreover, the distal-end axial portion 1621 and the fixing member body 1611 abut against each other when the first movable member 162 moves upward with respect to the fixing member 161, to prevent the first movable member 162 from popping off from the fixing member 161.

The pressing member 163 is a part receiving a depression operation (suction operation) by a doctor or the like, formed in a substantially cylindrical shape coaxial with the cylindrical member 151, and has an outer diameter that is smaller than an inner diameter of the cylindrical member 151 and larger than an outer diameter of the first movable member 162. This pressing member 163 is fixed to an upper end of the first movable member 162.

That is, the first movable member 162 is structure to be movable along the center axis Ax4 together with the pressing member 163 in response to the depression operation to the pressing member 163.

The second movable member 164 includes, as illustrated in FIG. 8 or FIG. 9, an airtight hat 1641, a balloon suction piston 1645, and two connecting rods 1646.

The airtight hat 1641 has an overall substantially cylindrical shape coaxial with the cylindrical member 151. This airtight hat 1641 includes, as illustrated in FIG. 8 or FIG. 9, a cylinder portion 1642, an inward jut-out portion 1643, and an outward jut-out portion 1644.

The cylinder portion 1642 is a cylindrical part coaxial with the cylindrical member 151, and has an inner diameter larger than the outer diameter of the proximal-end axial portion 1622 of the first movable member 162 and smaller than the inner diameter of the cylindrical member 151.

On an inner peripheral surface of this cylinder portion 1642, plural U-grooves 1642A that penetrate through from a lower end to an upper surface of the inward jut-out portion 1643 are formed around the center axis Ax4 at predetermined intervals as illustrated in FIG. 9.

Moreover, in the cylinder portion 1642, at positions respectively facing the balloon-suction insertion hole 1611E and the two connecting-rod insertion holes 1611F of the fixing member 161, a balloon suction hole 1642B and two connecting-rod insertion holes 1642C extending from the lower end toward the upper side are formed.

The inward jut-out portion 1643 is a ring-shaped part that juts out toward the center axis Ax4 from an upper end of the cylinder portion 1642, and has an inner diameter a little larger than the outer diameter of the first movable member 162.

The outward jut-out portion 1644 is a ring-shaped part that juts out toward a direction opposite to the center axis Ax4 from a lower end of the cylinder portion 1642, and has an outer diameter smaller than an inner diameter of the cylindrical member 151 (the metal cylinder 1512).

On an outer peripheral surface of this outward jut-out portion 1644, an O-ring gasket 1644A is fit into one piece.

To this airtight hat 1641, the first movable member 162 is inserted. Moreover, the airtight hat 1641 is structured such that a gasket 1644A is movable along the center axis Ax4 while sliding on an inner peripheral surface of the cylindrical member 151 (the metal cylinder 1512) in a state in which the suction button 14 is attached to the fitting part 85. At this time, the outward jut-out portion 1644 and the jut-out portion 1612 abut against each other when the airtight hat 1641 (the second movable member 164) moves downward with respect to the fixing member 161, to prevent the second movable member 164 from falling off from the fixing member 161. Moreover, the balloon suction piston 1645 (a large-diameter axial portion 1645B described later), a stop plate 1647 described later, and the fixing member body 1611 abut against each other when the airtight hat 1641 (the second movable member 164) moves upward with respect to the fixing member 161, to prevent the second movable member 164 from popping off from the fixing member 161.

Furthermore, in a state in which the suction button 14 is attached to the fitting part 85, space (hereinafter, a third space A3 (FIG. 8)) surrounded by the cylindrical member 151, the fixing member 161, and the airtight hat 1641 is to be a channel in which fluid flows. That is, in a state in which the suction button 14 is removed from the fitting part 85 and the suction first and second units 15, 16 are separated from each other, part of the channel (the third space A3) is exposed to the outside as illustrated in FIG. 9.

The balloon suction piston 1645 has an overall substantially cylindrical shape extending along the center axis Ax4. The balloon suction piston 1645 is inserted in the balloon-suction insertion hole 1611E of the fixing member 161, and is fit in the balloon suction hole 1642B of the airtight hat 1641 at an upper end portion. Moreover, a lower end portion of the balloon suction piston 1645 is inserted in the communication channel 83 of the suction cylinder 8 in a state in which the suction button 14 is attached to the fitting part 85. That is, the balloon suction piston 1645 moves along with the airtight hat 1641, and is movable back and forth inside the communication channel 83 of the suction cylinder 8.

This balloon suction piston 1645 has a structure in which a distal-end axial portion 1645A, the large diameter axial portion 1645B, and a proximal-end axial portion 1645C are arranged in series from the lower side to the upper side as illustrated in FIG. 8 or FIG. 9.

The distal-end axial portion 1645A has an outer diameter smaller than the inner diameter of the small diameter portion 832 of the communication channel 83. On an outer peripheral surface of the distal-end axial portion 1645A, an O-ring gasket 1645D is attached.

The large diameter portion 1645B has an outer diameter a little smaller than the inner diameter of the large diameter portion 833 of the communication channel 83 and larger than the balloon-suction insertion hole 1611E of the fixing member 161.

The proximal-end axial portion 1645C has an outer diameter a little smaller than the inner diameter of the balloon-suction insertion hole 1611E. The proximal-end axial portion 1645C is inserted in the balloon-suction insertion hole 1611E, and an upper portion is fit in the balloon suction hole 1642B.

The two connecting rods 1646 have overall substantially cylindrical shape along the center axis Ax4 as illustrated in FIG. 8. Two pieces of the connecting rods 1646 are inserted in the two connecting-rod insertion holes 1611F of the fixing member 161, and respective upper portions are fit in the connecting-rod insertion holes 1642C of the airtight hat 1641. Moreover, in the two connecting rods 1646, the stop plate 1647 plate is attached into one piece by screws (not illustrated) at respective lower end portions protruding to the lower side of the fixing member 161 through the two connecting-rod insertion holes 1611F.

In the stop plate 1647, at positions respectively facing the through hole 1611B, the three through holes 1611D, the balloon-suction insertion hole 1611E, and the two connecting-rod insertion holes 1611F of the fixing member 161, a center hole 1647A in which the first movable member 162 is inserted, three through holes 1647B, a balloon-suction insertion hole 1647C in which the balloon suction piston 1645 is inserted, and two connecting-rod insertion holes 1647D in which the two connecting rods 1646 are respectively inserted are formed.

The outside spring member 165 is constituted of a compression coil spring, and is positioned inside the cylinder portion 1642, abutting on a lower surface of the pressing member 163 at one end, and abutting against an upper surface of the outward jut-out portion 1644 at the other end. The outside spring member 165 applies a pushing force to make the pressing member 163 and the second movable member 164 move apart from each other.

The inside spring member 166 is constituted of a compression coil spring having a larger pushing force than the outside spring member 165, and abuts on a lower surface of the inward jut-out portion 1643 at one end, and abuts on an upper surface of the fixing member body 1611 at the other end in a state in which the cylinder portion 1611C is positioned thereinside. The inside spring member 166 applies a pushing force to make the fixing member 161 and the second movable member 164 move apart from each other.

Connection State of Tubes by Endoscope Button

In the following, connection states of the tubes 6 by the endoscope button 10 when no operation is performed, when the leak hole 1221A is closed with a finger, when a one-level depression operation is performed, and when a two-level depression operation is performed are explained sequentially.

When No Operation is Performed

Figure 10:
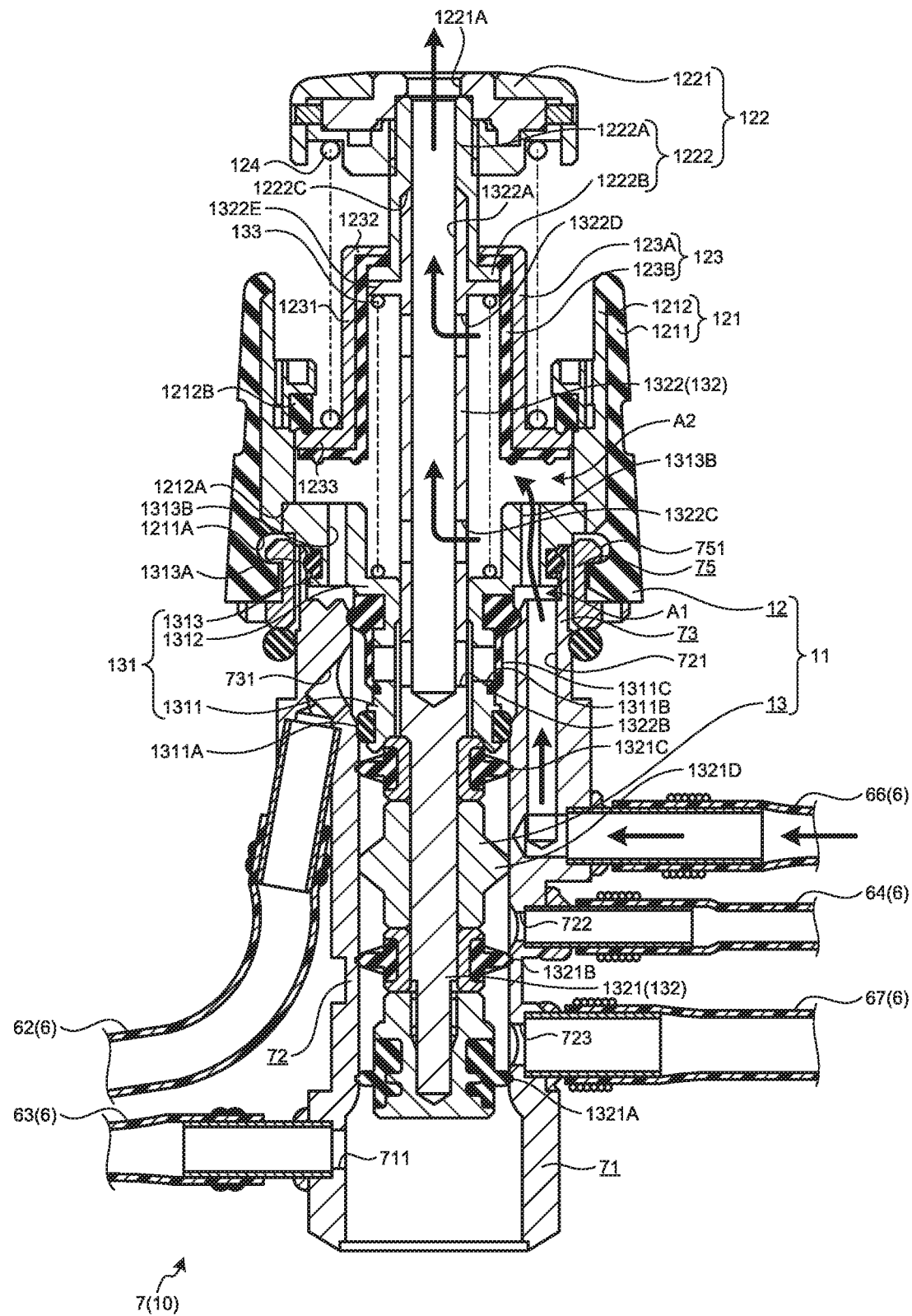
FIG. 10 illustrates a connection state of the tubes when an endoscope button is not operated.
Figure 11:
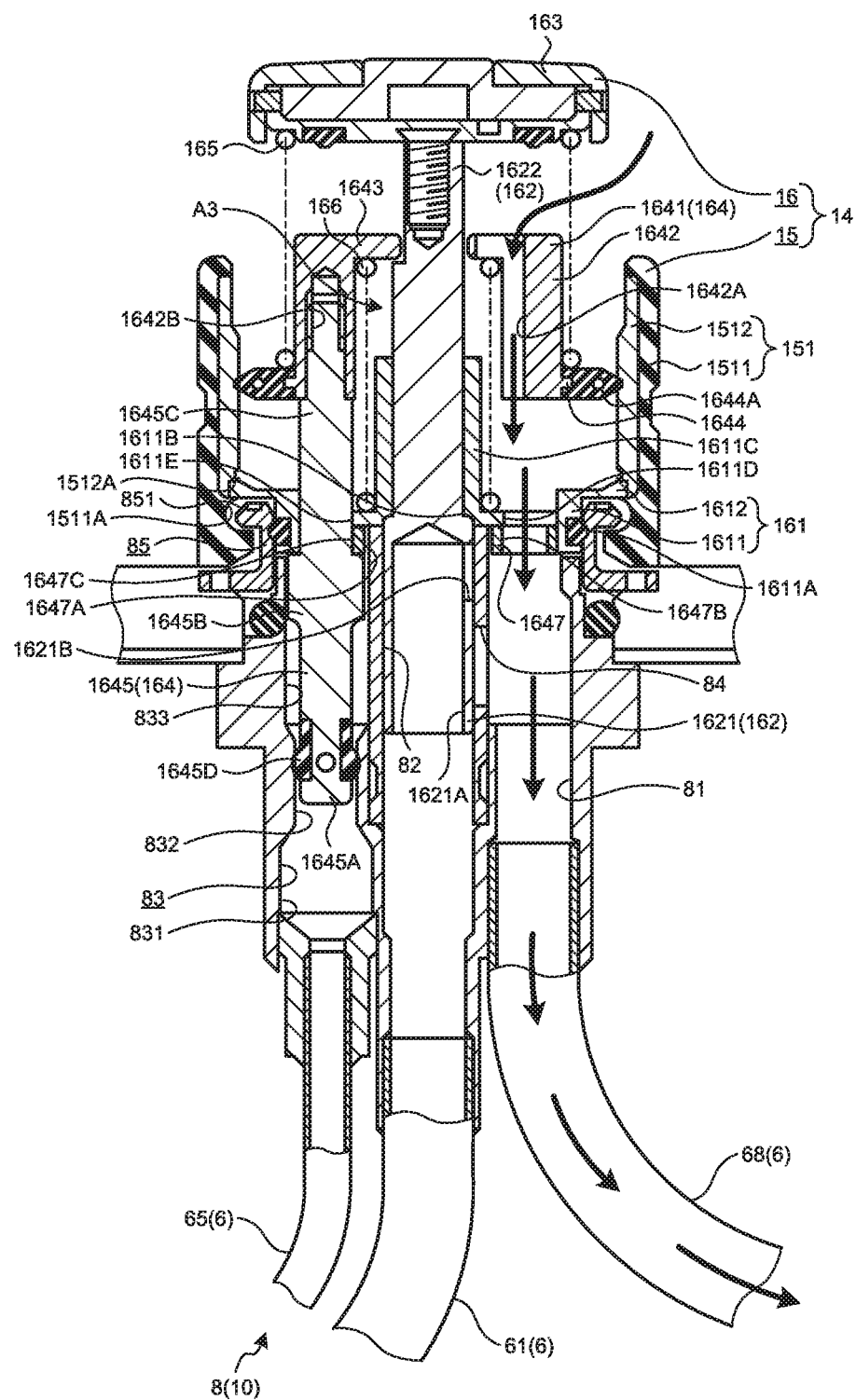
FIG. 11 illustrates a connection state of the tubes when the endoscope button is not operated.
Figure 12:
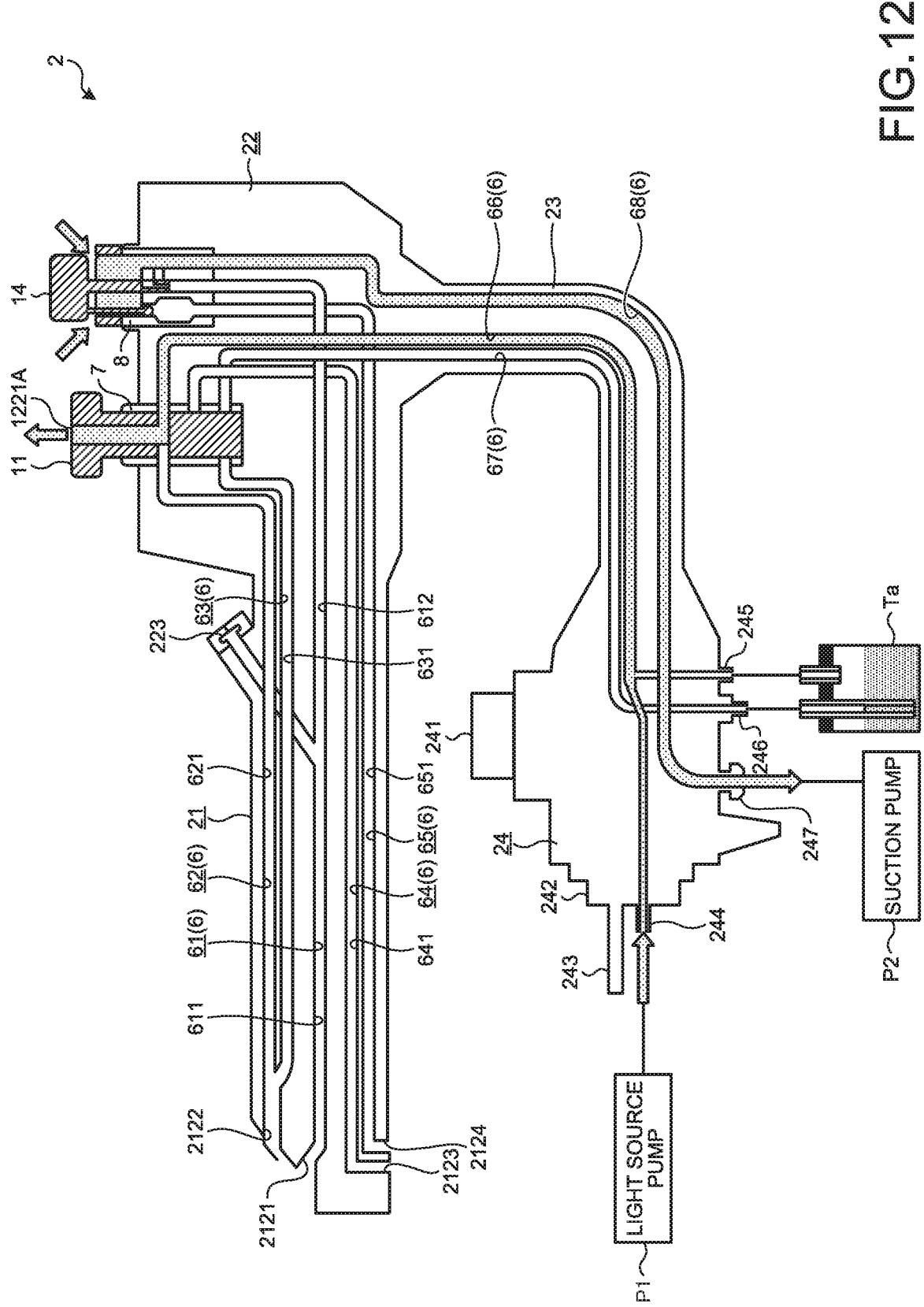
FIG. 12 illustrates a connection state of the tubes when the endoscope button is not operated.

FIG. 10 to FIG. 12 illustrate a connection state of the tubes when the endoscope button 10 is not operated. Specifically, FIG. 10 shows a connection state of the tubes 6 by the air/water supply button 11. FIG. 11 shows a connection state of the tubes 6 by the suction button 14. FIG. 12 is a diagram corresponding to FIG. 2.

When the air/water supply button 11 is not operated, air ejected from the light source pump P1 flows toward the air/water supply cylinder 7 through the proximal-end-side first tube 66. The air flowed toward the air/water supply cylinder 7 passes through, as indicated by arrows in FIG. 10, a passage of the communication path 721, the first space A1, the communication hole 1313B, the second space A2, the communication holes 1322C, 1322D, the bottomed axial hole 1322A, and to the leak hole 1221A, to be ejected to the outside of the ultrasound endoscope 2.

Moreover, when the suction button 14 is not operated, air outside the ultrasound endoscope 2 flows to the proximal-end-side third tube 68 as indicated by arrows in FIG. 11 with the driving of the suction pump P2, passing through a passage of the U-groove 1642A, the third space A3, the through hole 1611D (1647B), and to the communication channel 81. The air flowing through the proximal-end-side third tube 68 is sucked by the suction pump P2.

That is, when no operation is performed, the distal-end-side first to fifth tubes 61 to 65 and the proximal-end-side first to third tubes 66 to 68 are not to be connected with each other, as illustrated in FIG. 12, and any of air supply, water supply, and suction from a distal end of the insertion portion 21 is not performed.

When Leak Hole is Closed with Finger

Figure 13:
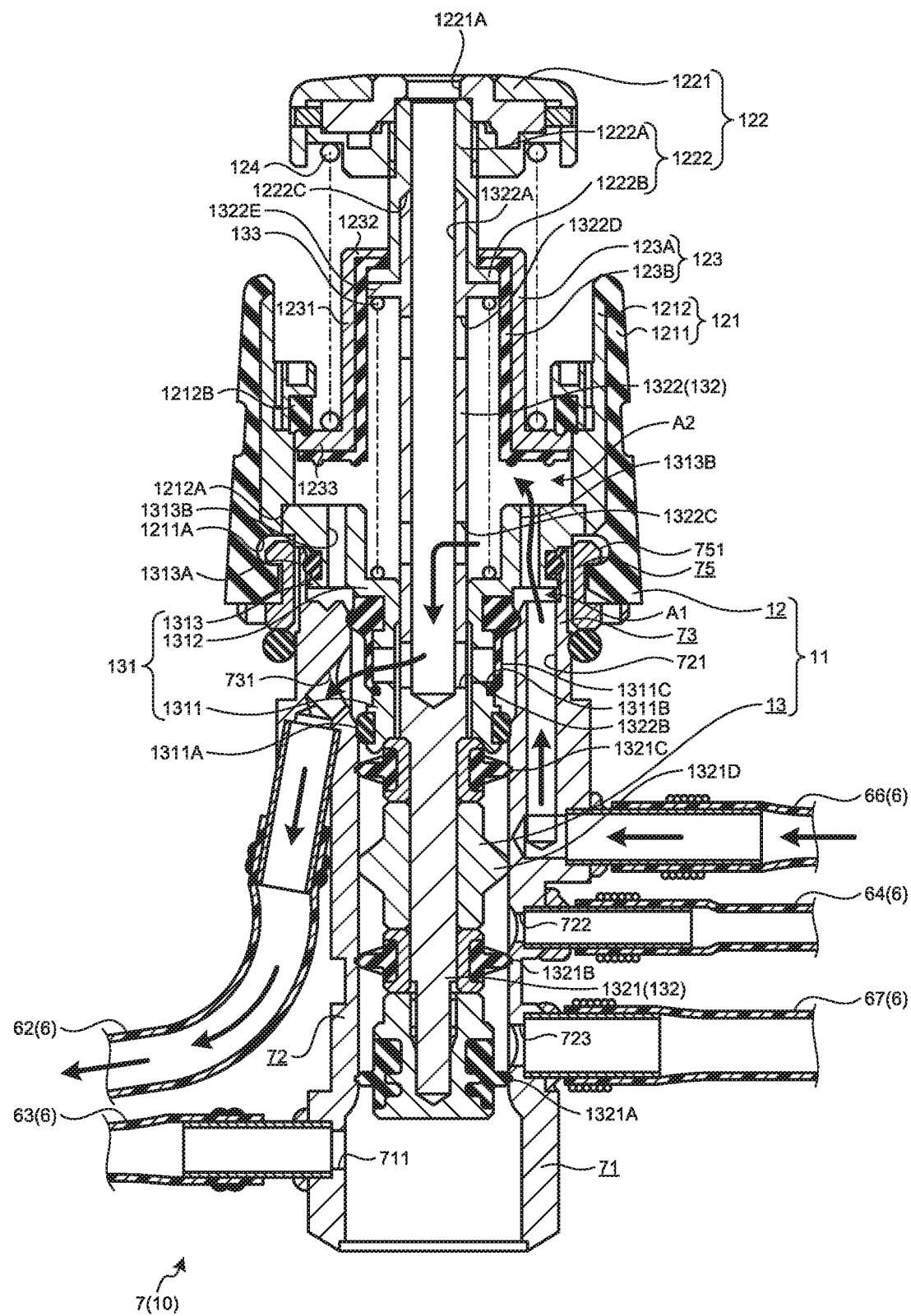
FIG. 13 illustrates a connection state of the tubes when a leak hole of the air/water supply button is closed with a finger.
Figure 14:
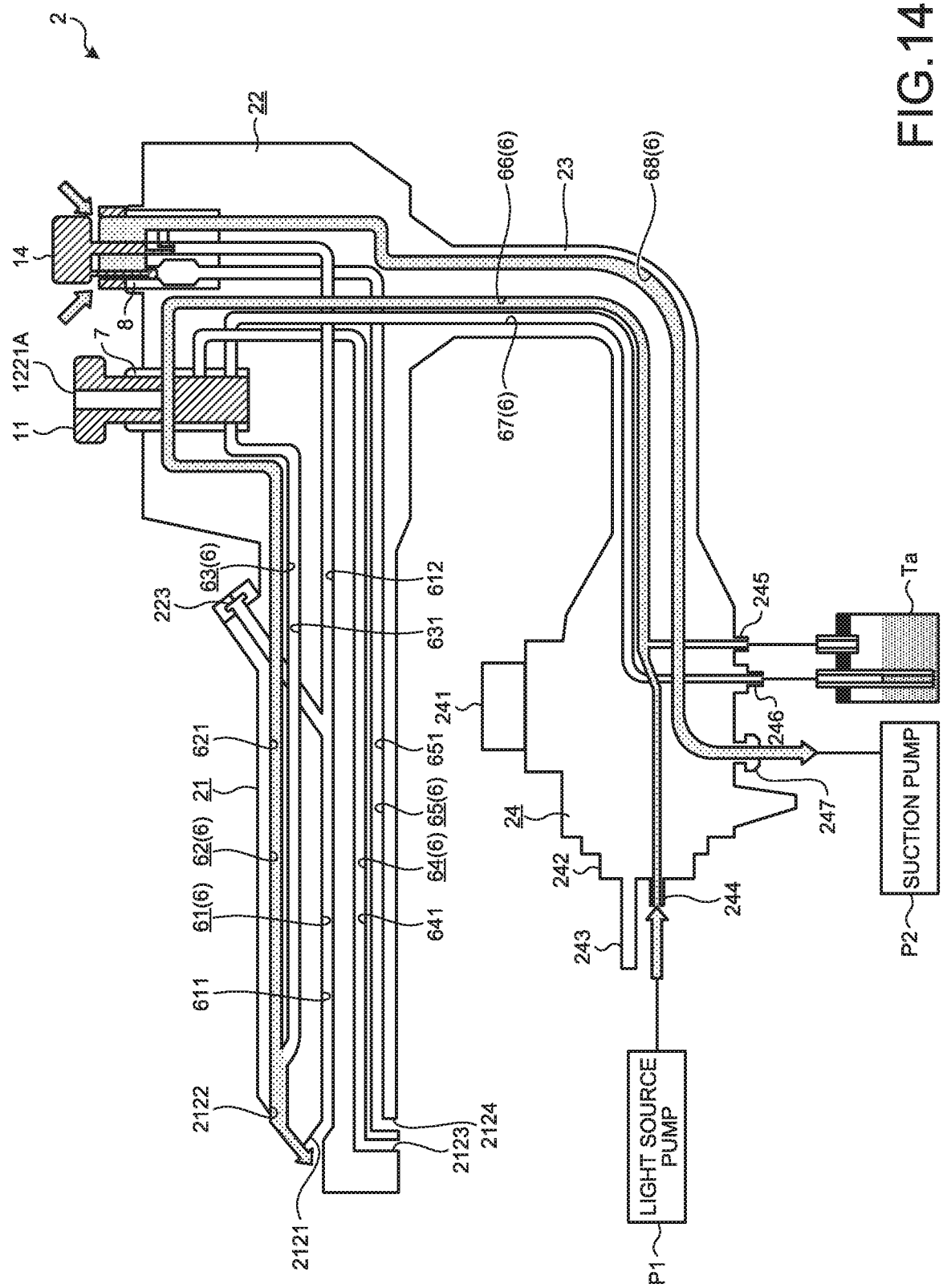
FIG. 14 illustrates a connection state of the tubes when the leak hole of the air/water supply button is closed with a finger.

FIG. 13 and FIG. 14 illustrate a connection state of the tubes 6 when the leak hole 1221A of the air/water supply button 11 is closed with a finger. Specifically, FIG. 13 is a diagram corresponding to FIG. 10. FIG. 14 is a diagram corresponding to FIG. 2. FIG. 14 shows a state in which the suction button 14 is not operated similarly to the case in FIG. 12.

When the leak hole 1221A is closed with a finger, an air pressure inside the bottomed axial hole 1322A increases, to open the check valve 1311C. As a result, air flowed into the bottomed axial hole 1322A flows to the distal-end-side second tube 62 passing through a passage of the communication holes 1322B, 1311B to the communication path 731 as indicated by arrows in FIG. 13. The air flowed in to the distal-end-side second tube 62 is ejected to the objective optical system (not illustrated) in an imaging hole (not illustrated) from the air/water supply hole 2122 as illustrated in FIG. 14.

When One-Level Depression Operation is Performed

Figure 15:
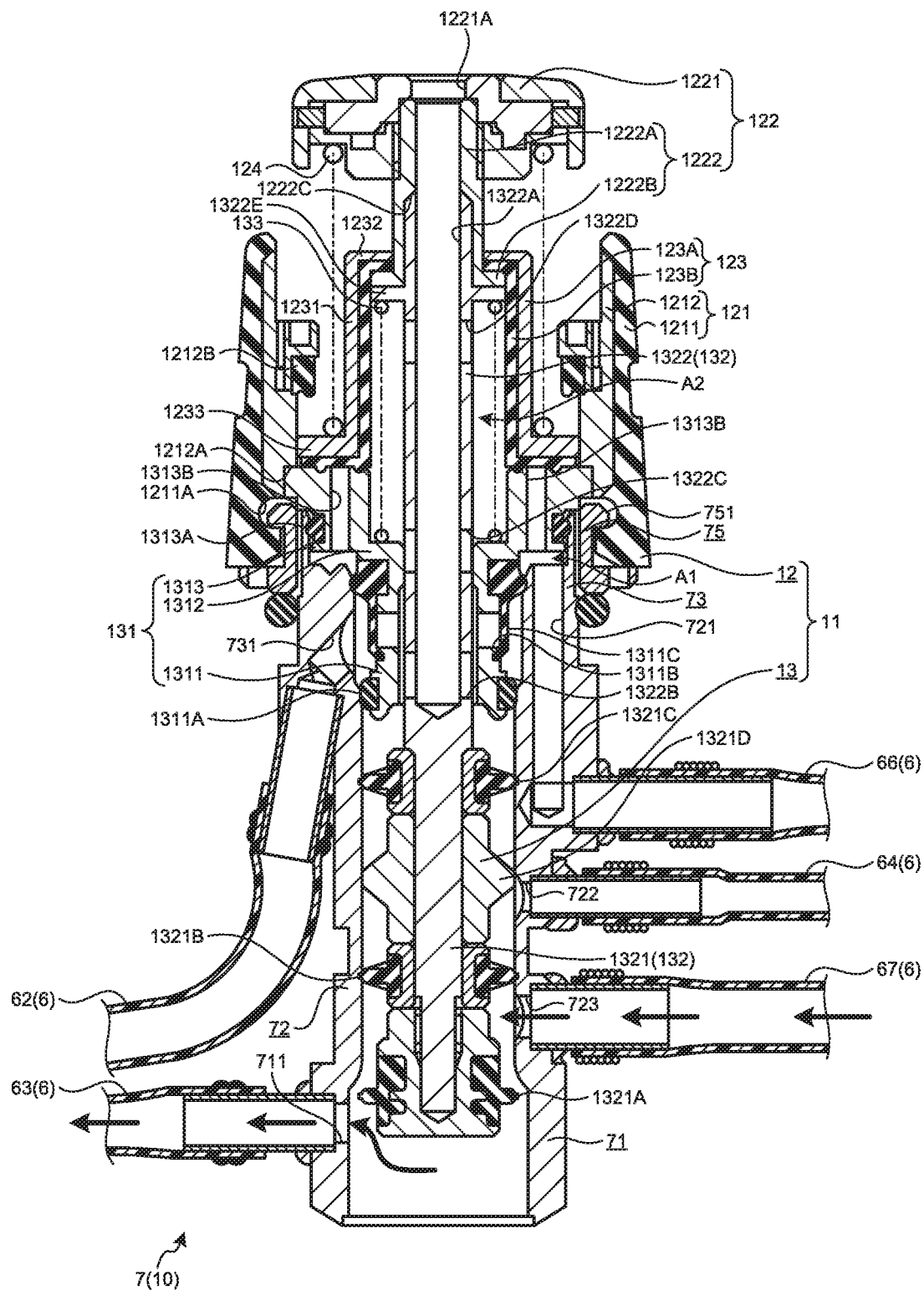
FIG. 15 illustrates a connection state of the tubes when a one-level depression operation is performed with respect to the endoscope button.
Figure 16:
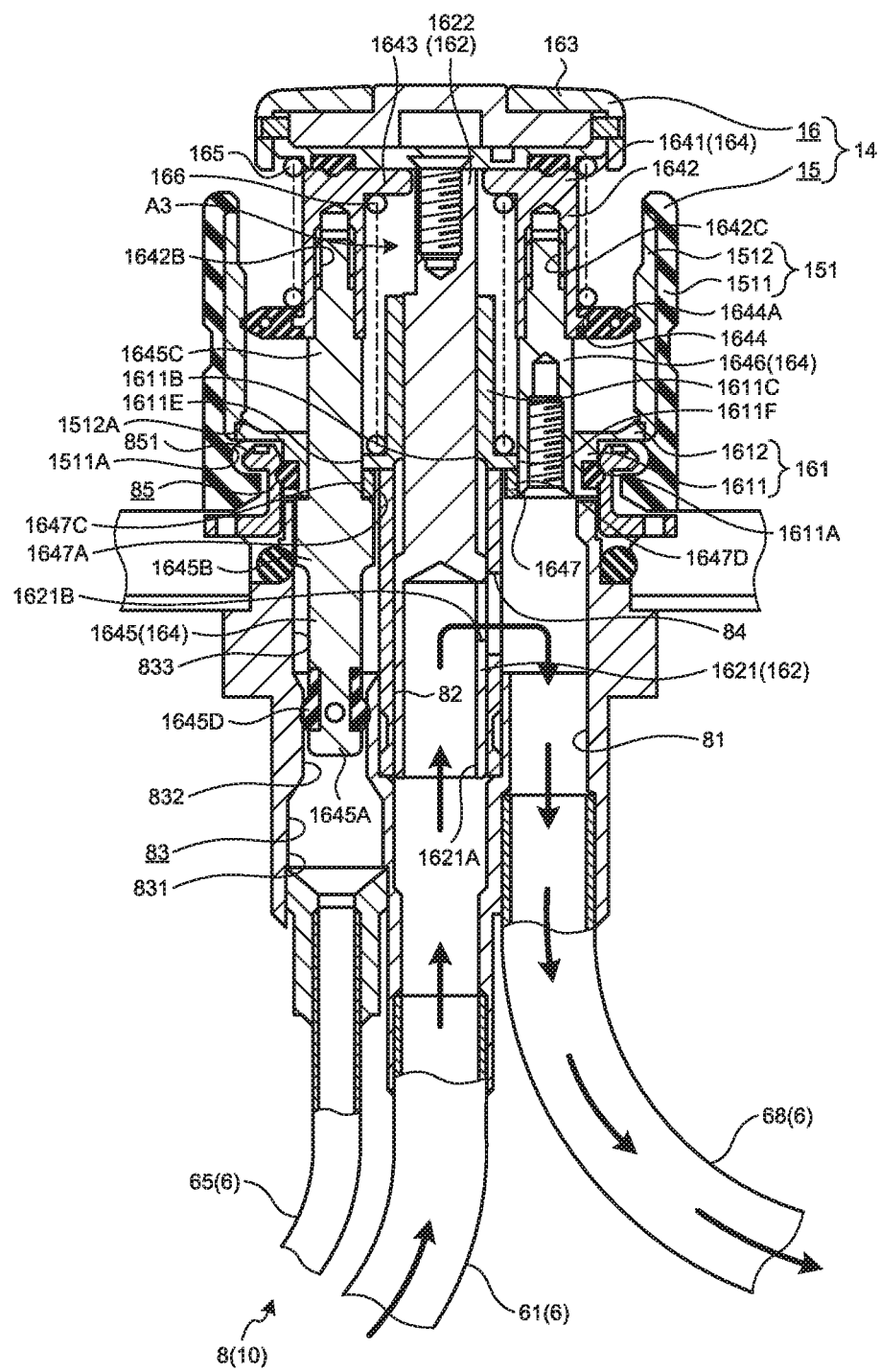
FIG. 16 illustrates a connection state of the tubes when the one-level depression operation is performed with respect to the endoscope button.
Figure 17:
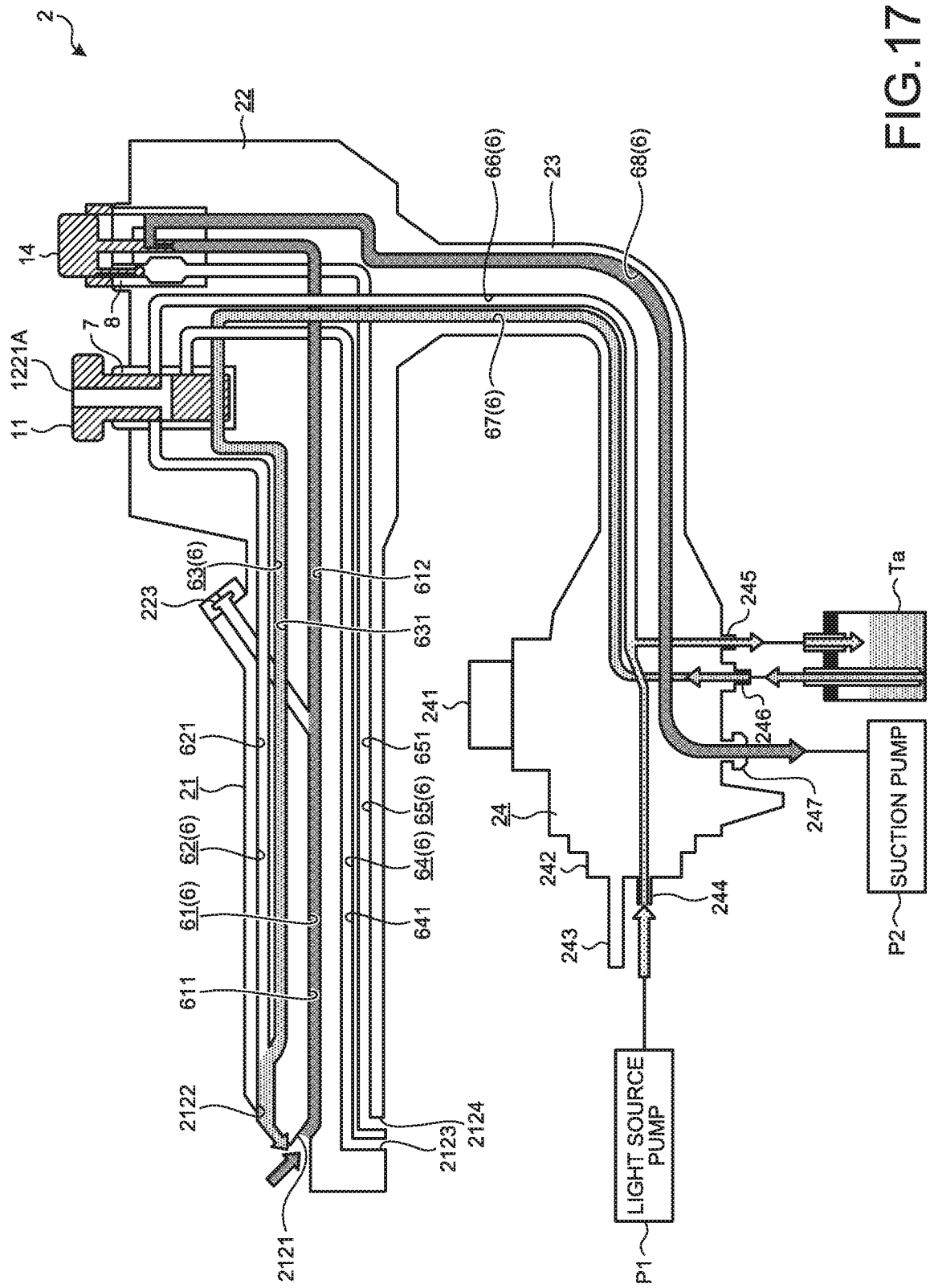
FIG. 17 illustrates a connection state of the tubes when the one-level depression operation is performed with respect to the endoscope button.

FIG. 15 to FIG. 17 illustrate a connection state of the tubes 6 when the one-level depression operation of the endoscope button 10 is performed. Specifically, FIG. 15 is a diagram corresponding to FIG. 10. FIG. 16 is a diagram corresponding to FIG. 11. FIG. 17 is a diagram corresponding to FIG. 2.

When the air/water supply button 11 is depressed one level, according to the magnitude relationship in the pushing force of the outside spring member 124 and the inside spring member 133, only the inside spring member 133 is compressed, and the pressing member 122, the second movable member 123, and the first movable member 132 integrally move downward as illustrated in FIG. 15. When the lower surface of the outward jut-out portion 1233 abuts on the upper surface of the large diameter portion 1313, the downward movement of the pressing member 122, the second movable member 123, and the first movable member 132 stops. That is, the communication hole 1313B is closed with the lower surface of the outward jut-out portion 1233.

Therefore, air ejected out from the light source pump P1 flows into the water supply tank Ta through the proximal-end-side first tube 66 as illustrated in FIG. 17 to apply pressure to the inside of the water supply tank Ta, and water flows out from the water supply tank Ta. The water from the water supply tank Ta flows toward the air/water supply cylinder 7 through the proximal-end-side second tube 67.

With the downward movement of the first movable member 132, the first gasket 1321A is released from contact with the inner peripheral surface of the sliding cylinder portion 72, to enter inside the lower-end cylinder portion 71. That is, in the air/water supply cylinder 7, a state in which the communication paths 711, 723 communicate with each other is obtained. Therefore, the water flowing toward the air/water supply cylinder 7 flows into the distal-end-side third tube 63, flowing through a passage of the communication path 723, the lower-end cylinder portion 71, and to the communication path 711. The water flowed in to the distal-end-side third tube 63 is ejected toward the objective optical system (not illustrated) in the imaging hole (not illustrated) from the air/water supply hole 2122 as illustrated in FIG. 17.

Furthermore, when the suction button 14 is depressed one level, according to the magnitude relationship in the pushing force of the outside spring member 165 and the inside spring member 166, only the outside spring member 165 is compressed, and the pressing member 163 and the first movable member 132 move downward, but not the second movable member 123 as illustrated in FIG. 16. When the lower surface of the pressing member 163 abuts on the upper surface of the airtight hat 1641 (the inward jut-out portion 1643), the downward movement of the pressing member 163 and the first movable member 162 stops. That is, the U-groove 1642A is closed with the lower surface of the pressing member 163.

With the downward movement of the first movable member 162, the communication holes 1621B, 84 come to the same position. Therefore, the distal-end-side first tube 61 and the proximal-end-side third tube 68 communicate with each other through a path of the communication channel 82, the bottomed axial hole 1621A, the communication holes 1621B, 84, and to the communication channel 81 as indicated by arrows in FIG. 16. Fluid in the subject flows into the distal-end-side first tube 61 from the treatment tool channel 2121 as illustrated in FIG. 17, and is sucked by the suction pump P2 through the path described above and the proximal-end-side third tube 68.

When Second-Level Depression Operation is Performed

Figure 18:
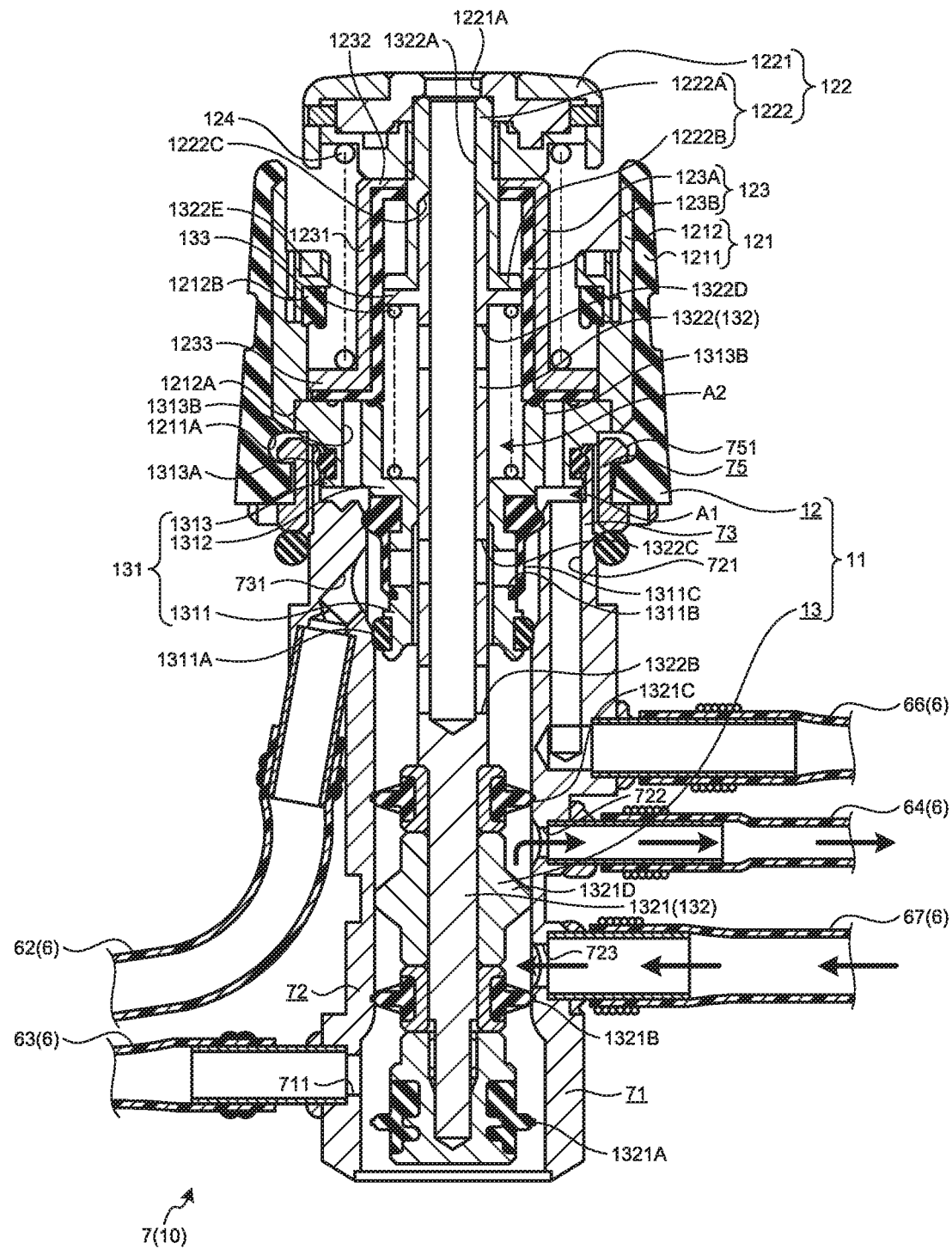
FIG. 18 illustrates a connection state of the tubes when a two-level depression operation is performed with respect to the endoscope button.
Figure 19:
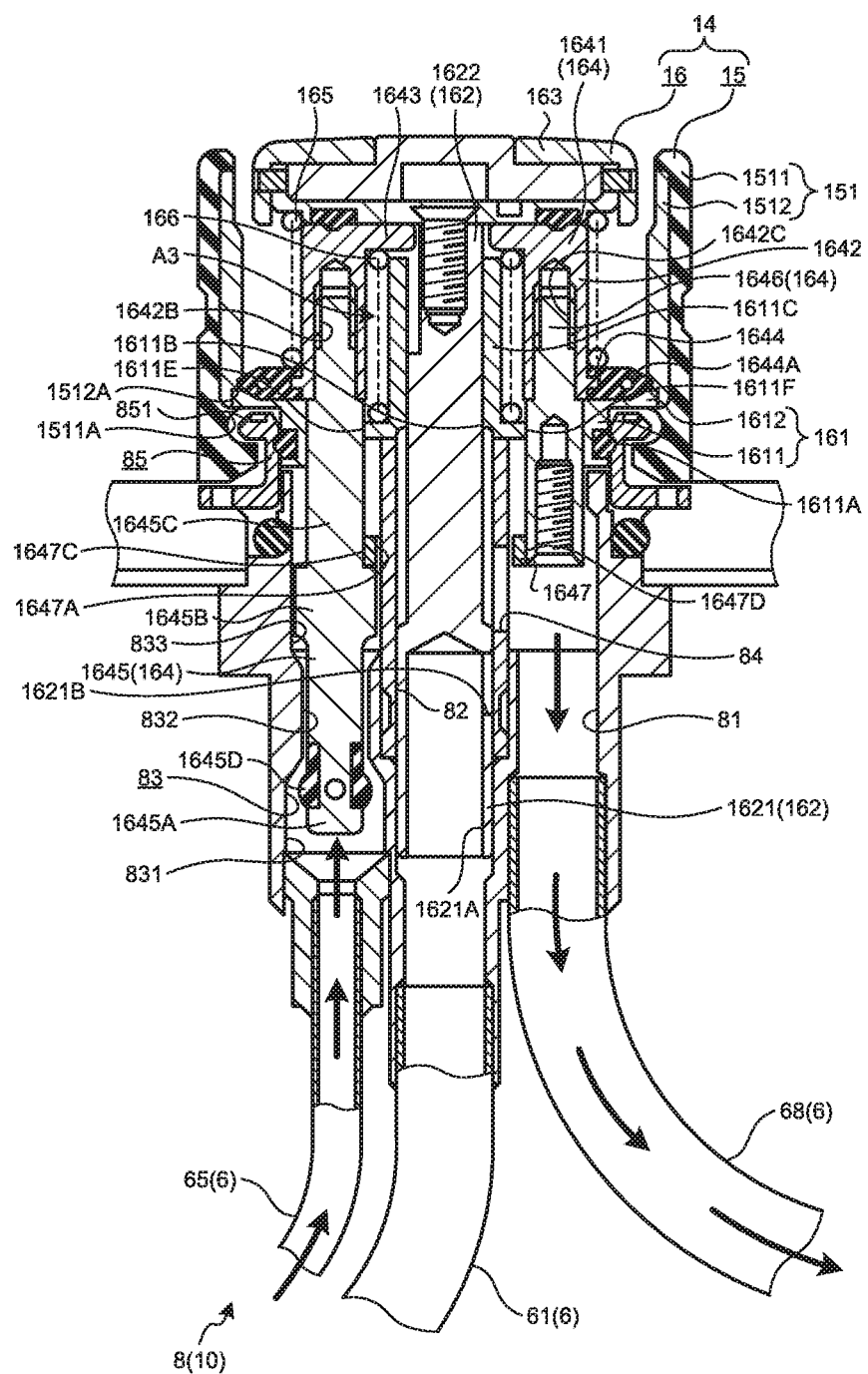
FIG. 19 illustrates a connection state of the tubes when the two-level depression operation is performed with respect to the endoscope button.
Figure 20:
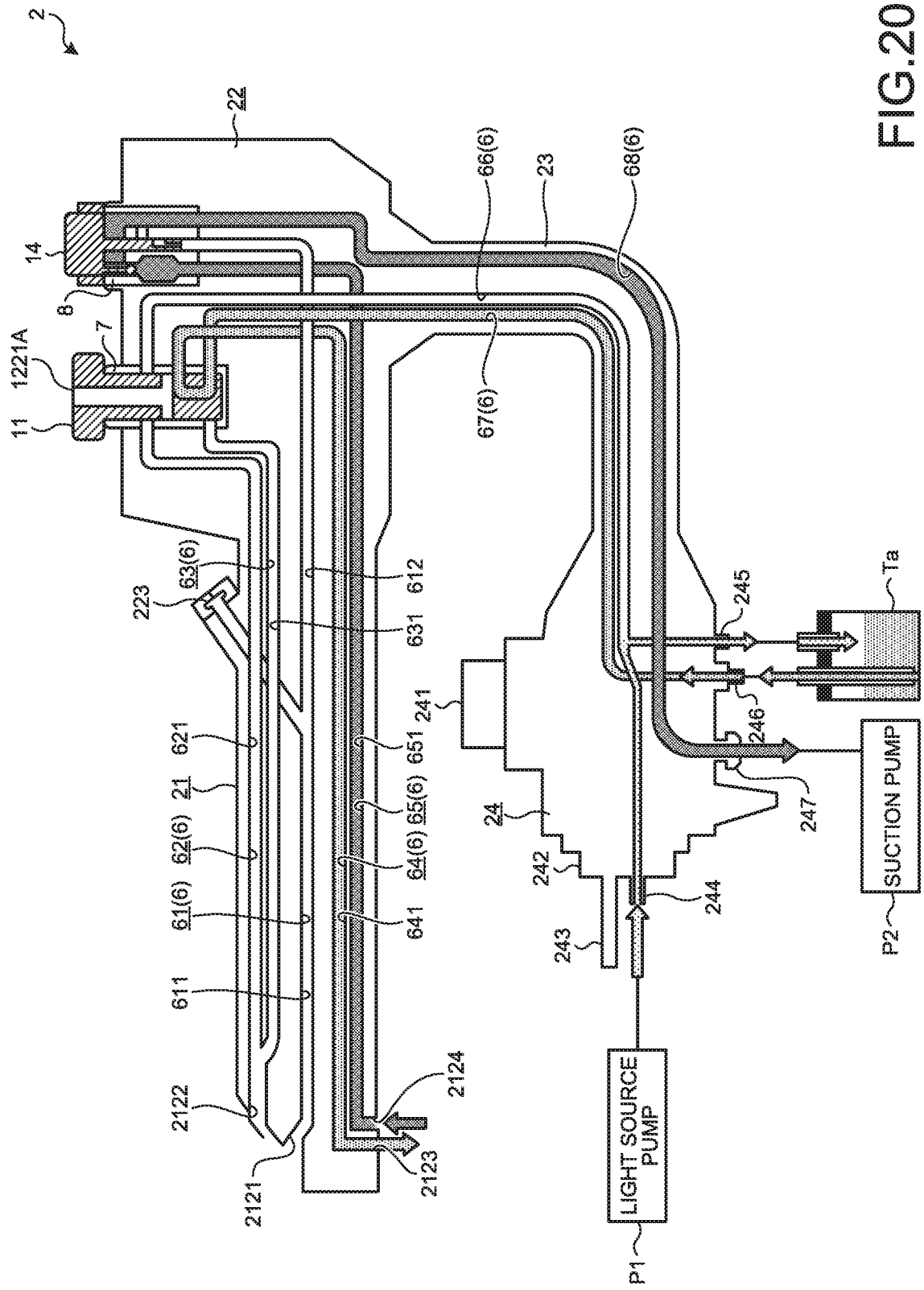
FIG. 20 illustrates a connection state of the tubes when the two-level depression operation is performed with respect to the endoscope button.

FIG. 18 to FIG. 20 illustrate a connection state of the tubes 6 when the two-level depression operation of the endoscope button 10 is performed. Specifically, FIG. 18 is a diagram corresponding to FIG. 10. FIG. 19 is a diagram corresponding to FIG. 11. FIG. 20 is a diagram corresponding to FIG. 2.

When the air/water supply button 11 is depressed two levels (when the depression operation is performed one more level further from the state illustrated in FIG. 15), the outside spring member 124 is compressed, and the pressing member 122 and the first movable member 132 integrally move downward, but not the second movable member 123 as illustrated in FIG. 18. When the lower surface of the pressing member 122 abuts on the upper surface of the second movable member 123, the downward movement of the pressing member 122 and the first movable member 132 stops.

With the downward movement of the first movable member 132, the second gasket 1321B moves below the communication path 723 inside the sliding cylinder portion 72.

That is, a state in which the communication paths 711, 723 are separated from each other by the second gasket 1321B and the communication paths 722, 723 communicate with each other through the communicating pivotal member 1321D is obtained. Therefore, the water flowing toward the air/water supply cylinder 7 flows into the distal-end-side fourth tube 64, flowing through a passage of the communication path 723, the communicating pivotal member 1321D, and to the communication path 722. The water flowed in to the distal-end-side fourth tube 64 is filled in a balloon (not illustrated) through the water supply hole 2123 as illustrated in FIG. 20.

When the suction button 14 is depressed two levels (when the depression operation is performed one more level further from the state illustrated in FIG. 16), the inside spring member 166 is compressed, and the pressing member 163, the first movable member 162, and the second movable member 164 integrally move downward as illustrated in FIG. 19. When the lower surface of the airtight hat 1641 (the outward jut-out portion 1644) abuts on the upper surface of the jut-out portion 1612, the downward movement of the pressing member 163, the first movable member 162, and the second movable member 164 stops.

With the downward movement of the first movable member 162, the positions of the communication holes 1621B, 84 are displaced as illustrated in FIG. 19, and the communication channels 81, 82 are separated from each other. Moreover, with the downward movement of the balloon suction piston 1645 (the second movable member 164), the gasket 1645D is released from contact with the inner peripheral surface of the small diameter portion 832 to enter inside the expanded diameter portion 831. That is, in the suction cylinder 8, a state in which the communication channels 81, 82 communicate with each other is obtained. Therefore, the water in the balloon (not illustrated) flows into the distal-end-side fifth tube 65 from the suction hole 2124 as illustrated in FIG. 20, and is sucked by the suction pump P2 through the communication channels 81, 82, and the proximal-end-side third tube 68.

In the endoscope button 10 according to the present embodiment explained above, the air/water supply button 11 is constituted of two units, the air/water supply first and second units 12, 13 that can be separated from each other. Similarly, the suction button 14 is constituted of two units, the suction first and second units 15, 16 that can be separated from each other. That is, when cleaning or sterilization of the air/water supply button 11 is to be performed, the air/water supply first and second units 12, 13 are separated from each other, and cleaning or sterilization can be performed separately per unit for the air/water supply first and second units 12, 13. The same applies to the suction button 14.

Particularly, by separating the air/water supply first unit 12 (the cylindrical member 121) from the air/water supply second unit 13, part of the internal channel (the second space A2) can be exposed to outside. Similarly, by separating the suction first unit 15 (the cylindrical member 151) from the suction second unit 16, part of the internal channel (the third space A3) can be exposed to outside.

Therefore, in the endoscope button 10 according to the present embodiment, a structure easy to put cleaning solution or antiseptic solution into the internal channels can be achieved. Therefore, it is possible to avoid spending unnecessarily long time for cleaning and sterilization.

From the above, according to the endoscope button 10 according to the present embodiment, an effect that work time for cleaning and sterilization can be reduced is produced.

Moreover, the endoscope button 10 according to the present embodiment is structured to be separated into two units. Because it is separated into two units, the assembly process is easy, while assembling with the fitting parts 75, 85 after cleaning and sterilization can be complicated if it is disassembled into multiple parts.

Particularly, the air/water supply second unit 13 is integrated with the air/water supply first unit 12 as the fixing member 131 engages with the concave portion 1212A when the cylindrical member 121 is attached to the fitting part 75, an is separated from the air/water supply first unit 12 as engagement between the fixing member 131 and the concave portion 1212A is released when the cylindrical member 121 is removed from the fitting part 75. Similarly, the suction second unit 16 is integrated with the suction first unit 15 as the fixing member 161 engages with the concave portion 1512A when the cylindrical member 151 is attached to the fitting part 85, and is separated from the suction first unit 15 as the engagement between the fixing member 161 and the concave portion 1512A is released when the cylindrical member 151 is removed from the fitting part 85.

By adopting such an engagement structure of the fixing members 131, 161 and the concave portion 1212A, 1512A, the separation process into two units of the endoscope button 10 and assembly process with the fitting parts 75, 85 of the endoscope button 10 become significantly simple.

Moreover, in the endoscope button 10 according to the present embodiment, a structure in which the connection state of the multiple tubes 6 is switched by the two-level depression operation is adopted. In such a structure, the internal structure of the endoscope button 10 becomes significantly complicated as described above.

By adopting the structure enabled to be separated into two units as in the endoscope button 10 according to the present embodiment, the effect that "work time for cleaning and sterilization can be reduced" described above can be preferably achieved.

Other Embodiments

The form to implement the present disclosure has been explained, but the present disclosure is not to be limited to the embodiment described above.

The endoscope button 10 according to the embodiment described above is enabled to be separated into two units 12, 13 (15, 16) by adopting the engagement structure of the fixing member 131 (161) and the concave portion 1212A (1512A), but it is not limited thereto. For example, the two units 12, 13 (15, 16) can be detachably structured.

In the endoscope button 10 according to the embodiment described above, the structure of switching the connection state of the multiple tubes 6 by the two-level depression operation is adopted, but not limited thereto, a structure in which only a one-level depression operation can be performed can be adopted.

In the embodiment described above, the endoscope system 1 has both the function of generating an ultrasound image and the function of generating an endoscopic image, but not limited thereto, it can be configured to have only the function of generating an ultrasound image.

In the embodiment described above, the endoscope system 1 can be an endoscope system that observes an inside of a subject, such as a mechanical structure, in an industrial field, not limited to the medical field.

According to the endoscope button, because at least part of a channel is exposed outside, it is easy to put cleaning solution or antiseptic solution therein. This produces an effect that work time for cleaning and sterilization is reduced.

Additional advantages and modifications will readily occur to those skilled in the art. Therefore, the disclosure in its broader aspects is not limited to the specific details and representative embodiments described herein. Accordingly, various modifications may be made without departing from the spirit or scope of the general inventive concept as defined by the appended claims and their equivalents.

What is claimed is:

1. A valve for an endoscope, the valve comprising: a first valve body and a second valve body each attachable and detachable with respect to a fitting part fixed to a cylinder of the endoscope, the first valve body and the second valve body being separable from each other in a state of being removed from the fitting part, wherein the first valve body includes a cylindrical member attachable and detachable with respect to the fitting part, the second valve body includes: a fixing member inserted inside the cylindrical member in a state in which the second valve body is attached to the fitting part, such that the fixing member is fixed to the cylindrical member; and a first movable member movably disposed with respect to the fixing member, the first movable member being movable back and forth inside the cylinder in the state in which the second valve body is attached to the fitting part; wherein the fixing member and the cylindrical member are configured such that the fitting part is disposed between the fixing member and the cylindrical member in a radial direction of the cylinder when the first valve body and the second valve body are attached to the fitting part.

2. The valve according to claim 1, further comprising, inside the valve, a channel, through which fluid can flow through, is formed when the first unit valve body and the second valve body are assembled with each other, at least a part of the channel exposing an outside of the endoscope when the first valve body and the second valve body are separated from each other.

3. The valve according to claim 1, further comprising an engaging portion that engages with the fixing member when the cylindrical member is attached to the fitting part to fix the fixing member, the engaging portion being arranged on an inner peripheral surface of the cylindrical member, wherein
the second valve body is integrated with the first valve body as the fixing member and the engaging portion engage with each other when the cylindrical member is attached to the fitting part, and is separated from the first valve body as engagement between the fixing member and the engaging portion is released when the cylindrical member is removed from the fitting part.

4. The valve according to claim 1, wherein
the valve is an air/water supply valve that accepts an air/water supply operation as a depression operation,
the first valve body is inserted inside the cylindrical member movably with respect to an inner peripheral surface of the cylindrical member, and includes a pressing member that accepts an air/water supply operation, and
the first movable member engages with the pressing member in a state in which the valve is attached to the fitting part, and is movable back and forth inside the cylinder, interlocking with the pressing member.

5. The valve according to claim 4, wherein the first valve body includes a second movable member movably attached with respect to an inner peripheral surface of the cylindrical member, the pressing member is movably attached with respect to the second movable member, and the valve switches a connection state of tubes in fluid communication with the cylinder by movement of at least one of the first movable member and the second movable member caused by a two-level depression operation.

6. The valve according to claim 1, wherein the valve is a suction valve that accepts a suction operation as a depression operation, and the second valve body includes a pressing member fixed with respect to the first movable member, and that accepts the suction operation.

7. The valve according to claim 6, wherein the second valve body includes a second movable member movably attached with respect to the fixing member, and is movable back and forth inside the cylinder in a state in which the second valve body is attached to the fitting part, and the valve switches a connection state of tubes in fluid communication with the cylinder by movement of at least either one of the first movable member and the second movable member caused by a two-level depression operation.

8. An endoscope comprising:

tubes configured to flow fluid therethrough;

an endoscope main body including
- a cylinder communicating with the tubes, and
- a fitting part fixed to the cylinder; and a valve including
- a first valve body and a second valve body each attachable and detachable with respect to the fitting part, the first valve body and the second valve body being separable from each other in a state of being removed from the fitting part, wherein
- the first valve body includes a cylindrical member attachable and detachable with respect to the fitting part,
- the second valve body includes:
   - a fixing member inserted inside the cylindrical member in a state in which the second valve body is attached to the fitting part such that the fixing member is fixed to an inner peripheral surface of the cylindrical member; and
   - a first movable member movably disposed with respect to the fixing member, the first movable member being movable back and forth inside the cylinder in the state in which the second valve body is attached to the fitting part;

wherein the fitting part is disposed between the fixing member and the cylindrical member in a radial direction of the cylinder.

9. An endoscope main body adapted to be attached to a valve that is able to be separable into a first valve body and a second valve body, the first valve body including a cylindrical member; the second valve body including a fixing member and a first movable member movably disposed with respect to the fixing member, the endoscope main body comprising:

tubes configured to flow fluid therethrough;

a cylinder to which the first movable member of the second valve body is attached thereinside, the cylinder communicating with the tubes, and a fitting part to and from which the fixing member of the second valve body is attachable and detachable, the fitting part being fixed to the cylinder;

wherein the fitting part is disposed between the fixing member and the cylindrical member in a radial direction of the cylinder.

10. An endoscope system for enabling liquid to flow, the endoscope system comprising:

a valve that is able to be separable into a first valve body and a second valve body, the first valve body including a cylindrical member; the second valve body including a fixing member and a first movable member movably disposed with respect to the fixing member;

an endoscope main body including:

tubes configured to flow fluid therethrough;

a cylinder to which the first movable member of the second valve body is attached thereinside, the cylinder communicating with the tubes, and a fitting part to and from which the fixing member of the second valve body is attachable and detachable, the fitting part being fixed to the cylinder;

a pump configured to eject air or water through the tubes; and a suction pump configured to apply a suction in the tubes;

wherein the fitting part is disposed between the fixing member and the cylindrical member in a radial direction of the cylinder.

* * * * *